US008835141B2

(12) United States Patent
Zhu et al.

(10) Patent No.: US 8,835,141 B2
(45) Date of Patent: Sep. 16, 2014

(54) METHODS FOR INTEGRATED CONVERSION OF LIGNOCELLULOSIC MATERIAL TO SUGARS OR BIOFUELS AND NANO-CELLULOSE

(75) Inventors: JunYong Zhu, Madison, WI (US); Ronald Sabo, Sun Prairie, WI (US); Craig Clemons, Madison, WI (US)

(73) Assignee: The United States of America as Represented by the Secretary of Agriculture, Washington, DC (US)

( * ) Notice: Subject to any disclaimer, the term of this patent is extended or adjusted under 35 U.S.C. 154(b) by 75 days.

(21) Appl. No.: 13/491,881

(22) Filed: Jun. 8, 2012

(65) Prior Publication Data
US 2012/0316330 A1 Dec. 13, 2012

Related U.S. Application Data

(60) Provisional application No. 61/495,190, filed on Jun. 9, 2011.

(51) Int. Cl.
C12P 19/14 (2006.01)
C08B 15/00 (2006.01)
B82Y 40/00 (2011.01)
C08H 7/00 (2011.01)
C08H 8/00 (2010.01)
C08B 37/00 (2006.01)

(52) U.S. Cl.
CPC .............. C08B 15/00 (2013.01); Y02E 50/16 (2013.01); B82Y 40/00 (2013.01); C08H 6/00 (2013.01); Y02E 50/343 (2013.01); C12P 19/14 (2013.01); C08H 8/00 (2013.01); Y02T 50/678 (2013.01); C08B 37/0024 (2013.01); C08B 37/0057 (2013.01); Y10S 977/795 (2013.01); Y10S 977/888 (2013.01)
USPC ............... 435/165; 435/99; 435/105; 435/96; 536/56; 977/795; 977/888

(58) Field of Classification Search
CPC ........... Y02E 50/16; C12P 19/14; C08H 8/00; B82Y 40/00; C08B 15/00; Y02T 50/678
USPC ......... 435/165, 99, 105, 96; 536/56; 977/795, 977/888
See application file for complete search history.

(56) References Cited

U.S. PATENT DOCUMENTS

| 4,650,689 | A | 3/1987 | Hedrick |
| 5,346,589 | A | 9/1994 | Braunstein |
| 5,562,777 | A | 10/1996 | Farone |
| 5,916,780 | A | 6/1999 | Foody |
| 7,514,247 | B2 | 4/2009 | Rush |
| 7,754,456 | B2 | 7/2010 | Penttila |
| 8,101,393 | B2 * | 1/2012 | Gray et al. .......... 435/209 |
| 2003/0054500 | A1 | 3/2003 | Ingram |
| 2006/0014260 | A1 | 1/2006 | Fan |
| 2006/0177917 | A1 | 8/2006 | Warzywoda |
| 2007/0152378 | A1 | 7/2007 | Kim |
| 2008/0044877 | A1 | 2/2008 | Penttila |
| 2009/0156868 | A1 | 6/2009 | Carter |
| 2009/0288788 | A1 | 11/2009 | Castor |
| 2009/0325252 | A1 | 12/2009 | Law |
| 2010/0003519 | A1 | 1/2010 | Chen |
| 2010/0146842 | A1 | 6/2010 | Dumenil |
| 2013/0000855 | A1 * | 1/2013 | Nuopponen et al. ............ 162/76 |

OTHER PUBLICATIONS

Aden A., et al, "Lignocellulosic Biomass to Ethanol Process Design and Economics Utilizing Co-Current Dilute Acid Prehydrolysis and Enzymatic Hydrolysis for Corn Stover", NREL, Jun. 2002, pp. 1-154.
Alemdar A., & Sain, M., "Isolated and Chracterization of Nanofibers from Agricultural Residues—Wheat Straw and Soy Hulls", Bioresource Technology, vol. 99, 2008, pp. 1664-1671.
Andresen M., Johansson L-S, Tanem B. S., Stenius P., "Properties and Characterization of Hydrophobized Microfibrillated Cellulose", 2006, vol. 13, Cellulose, pp. 665-677.
Zhang X, Qin W, Paice M. G., and Saddler J. N., "High Consistency Enzymatic Hydrolysis of Hardwood Substrates", Bioresource Technology, 2009, vol. 100, pp. 5890-5897.
Zhang Y. H. P. and Lynd L. R., "Toward an Aggregated Understanding of Enzymatic Hydrolysis of Cellulose: Noncomplexed Cellulase Systems", Biotechnology and Bioengineering, 2004, vol. 88, pp. 797-824.
Zhu J. Y., Pan X, Zalesny R. S. Jr., "Pretreatment of Wood Biomass for Biofuel Production: Energy Efficiency, Technologies, and Recalcitrance", Applied Microbiology and Biotechnology, 2010, vol. 87, pp. 847-857.
Chen Y., Liu C., Chang P. R., Cao X, and Anderson D. P., "Bionanocomposites Based on Pea Starch and Cellulose Nanowhiskers Hydrolyzed from Pea Hull Fibre: Effect of Hydrolysis Time", Carbohydrate Polymers, 2009, vol. 76, pp. 607-615.
"TAPPI Standard Test Method T230 om-99", TAPPI Test Methods, 2009.
Dong X. M., Revol J-F., and Gray D. G., "Effect of Microcrystallite Preparation Conditions on the Formation of Colloid Crystals of Cellulose", 1998, Cellulose, vol. 5, pp. 19-32.

(Continued)

Primary Examiner — Brandon Fetterolf
Assistant Examiner — Yih-Horng Shiao
(74) Attorney, Agent, or Firm — John D. Fado; Lesley D. Shaw; Janet I. Stockhausen

(57) ABSTRACT

The present invention relates to systems, compositions and methods for the conversion of lignocellulosic material to recalcitrant cellulose and hydrolyzed sugars and products produced therefrom (e.g., biofuel, nano-fibrillated cellulose). In particular, the invention provides novel fractionation processes configured to integrate production of hydrolyzed sugars (e.g., for biofuel production) and recalcitrant cellulose (e.g., for nano-fibrillated cellulose production) from lignocellulosic material and methods of using the same (e.g., in the production of biofuel and nano-fibrillated cellulose). The invention is also directed to nanocellulose with morphologies of having a less entangled and slightly branched fibril network, and having the same thermal stability as of that of the initial lignocellulose feedstock.

19 Claims, 40 Drawing Sheets

(56) References Cited

OTHER PUBLICATIONS

Farrell A. E., et al., "Ethanol Can Contribute to Energy and Environmental Goals", 2006, Science, vol. 311, 506-508.

Zhu J. Y., Pan X. J., "Woody Biomass Pretreatment for Cellulosic Ethanol Production: Technology and Energy Consumption Evaluation", Bioresource Technology, 2010, vol. 101, pp. 4992-5002.

Marchessault R. H., Morehead F. F., Koch M. J., "Some Hydrodynamtic Properties of Neutral Suspensions of Cellulose Crystallites as Related to Size and Shape", J. Colloid Science, 1961, vol. 16, pp. 327-344.

Hayashi N., Kondo T., and Ishihara M., "Enzymatically Produced Nano-Ordered Short Elements Containing Cellulose lb Crystalline Domains", Carbohydrate Polymers, Jun. 20, 2005, vol. 61, pp. 191-197.

Hendriks, A.T.W.M., & G. Zeeman., "Pretreatments to Enhance the Digestibility of Lignocellulosic Biomass", Bioresource Technology, 2009, vol. 100, pp. 10-18.

Henriksson M, Berglund L. A., Isakosson P, Lindstrom T, and Nishino T., "Cellulose Nanopaper Structures of High Toughness", Biomacromolecules, 2008, vol. 9, p. 1579-1585.

Henriksson M., Henriksson G., Berglund L. A., and Lindstrom T., "An Environmentally Friendly Method for Enzyme-Assisted Preperation of Microfibrillated Cellulose (MFC) Nanofibers", European Polymer Journal, 2007, vol. 43, pp. 3434-3441.

Himmel, M. E., et al., "Biomass Recalcitrance: Engineering Plants and Enzymes for Biofuels Production", Science, 2007, vol. 315, pp. 804-807.

Iwamoto S., Nakagaito A. N., and Yano. H., "Nano-Fibrillation of Pulp Fibers for The Processing of Transparent Nanocomposites", Applied Physics A, 2007, vol. 89, pp. 461-466.

Moran J. I., Alvarez V. A., Cyras V. P., and Vazquez A., "Extraction of Cellulose and Preparation of Nanocellulose from Sisal Fibers", Cellulose, 2008, vol. 15 pp. 149-159.

Wang B., Sain M., Oksman K., "Study of Structural Morphology of Hemp Fiber from the Micro to the Nanoscale", Applied Composite Materials, 2007, vol. 14, pp. 89-103.

Nakagaito A. N. & Yano. H., "The Effect of the Morphological Changes From Pulp Fiber Towards Nano-Scale Fibrillated Cellulose on the Mechanical Properties of High-Strength Plant Fiber Based Composites", Applied Physics A, 2004, vol. 78, pp. 547-552.

Nickerson R. F. & Harble J. A., "Cellulose Intercrustalline Structure", Industrial and Engineering Chemistry, 1947, vol. 39, pp. 1507-1512.

Okita Y., Saito T., and Isogai A., "TEMPO-Mediated Oxidation of Softwood Thermomechanical Pulp", Holzforschung, 2009, vol. 63, pp. 529-535.

Paakko, M., et al., "Enzymatic Hydrolysis Combined with Mechanical Shearing and High-Pressure Homogenization for Nanoscale Cellulos Fibrils and Strong Gels", Biomacromolecules, 2007, vol. 8, pp. 1934-1941.

Saito T. & Isogai A., "TEMPO-Mediated Oxidation of Native Cellulose. The Effect of Oxidation Conditions on Chemical and Crystal Structures of the Water-Insoluble Fractions", Biomacromolecules, 2004, vol. 5, pp. 1983-1989.

Saito T., Kimura S., Nishiyama Y., and Isogai A., "Cellulose of Nanofibers Prepared by TEMPO-Mediated Oxidation of Native Cellulose", Biomacromolecules, 2007, vol. 8, pp. 2485-2491.

Saito T., Okita Y., Nge T. T., Sugiyama J., and Isogai A., "TEMPO-Mediated Oxidation of Native Cellulose: Microscopic ANalysis of Fibrous Fractions in the Oxidized Products", Carbohydrate Polymers, 2006, vol. 65, pp. 435-440.

Scharlemann J. P. W. & Laurance W. F., "How Green are Biofuels", Science, 2008, vol. 319, pp. 43-44.

Siro I. & Plackett D.,, "Microfibrillated Cellulose and New Nanocomposite Materials: A Review", Cellulose, 2010, vol. 17, pp. 459-494.

Wegner T. H. & Jones E. P., "A Fundamental Review of the Relationships between Nanotechnology and Lignocellulosic Biomass", Nanoscience and Technology of Renewable Biomaterials, 2009, 1st Ed, 1-41.

Favier V., Chanzy H., and Cavaille JY., "Polymer Nanocomposites Reinforced by Cellulose Whiskers", Macromolecules, 1995, vol. 28, pp. 6365-6367.

Dufresne., Cavaille J-Y., and Vignon M., "Mechanical Behavior of Sheets Prepared from Sugar Beet Cellulose Microfibrils", J. Applied Polymer Science, 1997, vol. 64, pp. 1185-1194.

Pulp and Paper Manufacture, Eds. The Joint Text Book Committee of the Paper Industry,TAPPI, 1985, vol. 1-10, ISBN: 0-919893-04-X.

Papermaking Science and Technology, Eds. Gullichsen & Paulapuro, vol. 1-19, Fapet Oy, 2000, ISBN:952-5216-00-4.

Bondeson D., Matthrew A., and Oksman K., "Optimization of the Isolation of Nanocrystals from Microcrystalline Cellulose by Acid Hydrolysis", Cellulose, 2006, vol. 13, pp. 171-180.

TAPPI Test Methods, Technical Association of the Pulp and Paper Industry, 2009, Atlanta, GA.

Mazumder BB, et al., "Combination treatment of kenaf bast fiber for high viscosity pulp," J Wood Sci, 2000, 46:364-370.

Agarwal UP, et al., "Cellulose I crystallinity determination using FT-Raman spectroscopy: univariate and multivariate methods," Cellulose, 2010, 17:721-733.

Zhu JY, et al., "Integrated production of nano-fibrillated cellulose and cellulosic biofuel (ethanol) by enzymatic fractionation of wood fibers," Royal Soc Chem, 2011.

Zhu JY, et al., "Integrated Production of Nanocellulose with Biofuel," 2010 International Nano Technology Conference for the Forest Products Industry, Espoo, Finland, Sep. 27-29, 2010.

\* cited by examiner

US 8,835,141 B2

METHODS FOR INTEGRATED CONVERSION OF LIGNOCELLULOSIC MATERIAL TO SUGARS OR BIOFUELS AND NANO-CELLULOSE

The present application claims the benefit of U.S. Provisional Patent Application Ser. No. 61/495,190, filed Jun. 9, 2011, which is incorporated herein by reference in its entirety.

FIELD OF THE INVENTION

The present invention relates to systems, compositions and methods for the conversion of lignocellulosic material to recalcitrant cellulose and hydrolyzed sugars and products produced therefrom (e.g., sugars, biofuel, micro- and/or nano-fibrillated cellulose). In particular, the invention provides novel fractionation processes configured to integrate production of hydrolyzed sugars (e.g., for biofuel or chemical production) and recalcitrant cellulose (e.g., for micro- and/or nano-fibrillated cellulose production) from lignocellulosic material, and methods of using the same (e.g., in the production of biofuel and micro- and/or nano-fibrillated cellulose).

BACKGROUND OF THE INVENTION

Bioconversion of biomass to biofuel and bioproducts has great potential to transform the current petroleum based economy to a more sustainable biobased economy. It has been recognized that value added co-products are necessary for economic production of biofuel from plant biomass.

Micro- and nano-cellulose, derived from plant biomass are finding use in an ever-increasing number of applications, e.g., in the production of cellulose films, for use in combination with other materials (e.g., woods, plastics, coatings, adhesives) to alter or enhance strength, flexibility, or other mechanical properties. Thus, micro- and nano-cellulose can be a valuable co-product for biofuel, and vice versa.

Previous work on bioconversion of plant biomass has focused either on maximizing the conversion of cellulose to sugars for the production of fuels, or on maximizing the production of high-value nanofibrillated cellulose while minimizing saccharification.

SUMMARY OF THE INVENTION

The present invention provides integrated methods for producing both sugars (for fuels or chemicals) and recalcitrant cellulose (for use in producing micro- and/or nano-cellulose) in a single process from lignocellulosic materials such as plant biomass. Experiments conducted during the course of developing embodiments for the present invention demonstrated integration of the production of nano-cellulose, a highly valuable biomaterial, with the production of sugar/biofuel (e.g., ethanol) from lignocellulosic material (e.g., wood fibers). In particular, commercial cellulase enzymes were used to fractionate amorphous cellulose from lignocellulosic material (e.g., bleached kraft eucalyptus pulp) to yield a hydrolyzed sugar fraction and a highly crystalline recalcitrant cellulose fraction. The hydrolyzed sugars were found to be easily converted to biofuel (e.g., ethanol) through yeast fermentation with an efficiency of 91%.

A range of fractionation yields of recalcitrant cellulose may be achieved by varying hydrolysis duration and enzyme dosage. While recalcitrant cellulose is difficult to hydrolyze to sugars, and thus poses an obstacle in processes directed only to the production of biofuels, the recalcitrant cellulose was shown to be very suitable for producing biobased nanomaterials (e.g., nano-fibrillated cellulose) through, e.g., mechanical homogenization. In addition, the cellulose hydrolysis processes were shown to facilitate mechanical homogenization, e.g., to convert recalcitrant cellulose to nano-fibrillated cellulose, by significantly reducing the degree of polymerization (DP) of the recalcitrant cellulose (e.g., to approximately a DP of 400) and the length of the recalcitrant cellulose fibers (e.g., to about 200 μm). The crystallinity of the recalcitrant cellulose was found to be as much as 24% greater than that of the original bleached pulp. Films made from the generated nano-fibrillated cellulose were found to be optically transparent with opacity as low as 12%. The nano-fibrillated cellulose films were mechanically strong with tensile strength (maximum stress) and stiffness (modulus) of approximately 10 and 6 times higher, respectively, than those of film made of fibers without fibrillation.

Accordingly, the present invention relates to systems, compositions and methods for the conversion of lignocellulosic material to fractions comprising a) recalcitrant cellulose and b) hydrolyzed sugars, and products produced therefrom (e.g., biofuel, chemicals, micro and/or nano-fibrillated cellulose). In particular, the invention provides novel fractionation processes configured to integrate production of hydrolyzed sugars and recalcitrant cellulose from lignocellulosic material. In some embodiments, the present invention provides for the production of materials comprising a lignin component, e.g., micro and/or nano-lignocellulose fibers, and for materials produced therefrom.

The systems and methods of the present invention are not limited to the production of nano-cellulose (e.g., cellulose fibers, fiber networks or fibrous segments having diameters on the order of 1 μm or less). In some embodiments, the present invention provides systems and methods for the integrated production of sugars and microcrystalline cellulose. See, e.g., U.S. Pat. No. 5,346,589, which is incorporated herein by reference.

The present invention is not limited to particular methods for producing hydrolyzed sugar and recalcitrant cellulose. In some embodiments, the methods involve enzymatically hydrolyzing lignocellulosic material with a composition comprising one or more enzymes to produce a product comprising hydrolyzed sugars and recalcitrant cellulose, and partitioning the product such that a hydrolyzed sugar fraction is obtained and a recalcitrant cellulose fraction is obtained. In some embodiments, the composition comprising one or more enzymes comprises one or more cellulase enzymes, and/or hemicellulases to separate hemicelluloses from the recalcitrant cellulose (RC). In certain embodiments, the one or more enzymes comprise an enzyme selected from the group consisting of cellulase, complex cellulase of Genencor Multifect B, xylanase, endoxylanase, exoxylanase, beta xylosidase, endomannase, beta-mannosidase, beta-mannase, pectin lyase, pectate lyase, endopolygalacturonase, exopolygalacturonase, rhamnohydrolase, xylogalacturonase, alpha-rhamnosidase, rhamnogalacturonan lyase, xylosidase, arabinofuranosidase, arabinofuranohydrolase, endoarabinase, exoarabinase, endogalactanase, glucuronidase, feruloyl esterase, p-coumaroyl esterase, galactosidase, endoglucanase, exoglucanase, protease, lipase, glucoamylase, cellobiohydrolase, alpha amylase, acetyl esterase, methyl esterase, lignin peroxidase, and laccase. Enzymes may be natural, bioengineered or synthetic, or a combination thereof. In certain preferred embodiments, cellulase enzymes finding use in the present invention include one or more of endoglucanase, complex cellulase of Genencor Multifect B or other commercial complex cellulase, and/or exoglucanase, and/or a hemicellulase, and/or a combination of different single enzymes through advanced formulations.

In some embodiments, the methods further involve converting or fermenting (e.g., yeast fermenting) the hydrolyzed sugar fraction so as to generate a biofuel (e.g., alcohols and alkanes such as: ethanol, propanol, butanol, kerosene, jet fuel, etc.), or produce chemicals from sugars such as ethylene glycol (EG), propylene glycol (PG), butane glycol (BG). In some embodiments, the methods further involve processing, e.g., homogenizing, the recalcitrant cellulose fraction so as to generate micro- and/or nano-fibrillated cellose ("microcellulose" and/or "nanocellulose").

The methods are not limited to a particular form or type of lignocellulosic material. In some embodiments, the lignocellulosic material comprises one or more of virgin plant biomass, non-virgin plant biomass, agricultural biomass, commercial organics, construction and demolition debris, municipal solid waste, waste paper, and yard waste. In certain embodiments, virgin or non-virgin plant biomass comprises one or more of branches, stems, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet pulp, wheat middlings, oat hulls, hard and soft woods. In some particular embodiments, the lignocellulosic material comprises eucalyptus pulp. While not limiting the lignocellulosic material to any particular composition, in some embodiments, the lignocellulosic material comprises one or more of cellulose, hemicellulose, xylan, lignin, protein, beta-glucans, homogalacturonans, and rhamnogalacturonans.

In some embodiments, the methods of the invention are applied to lignocellulosic material is not chemically pretreated. In some embodiments, the invention provides a nanocellulose product produced without chemical pretreatment of the initial lignocellulosic material, wherein the cellulose has morphology that is less entangled, and that has a slightly branched fibril network. In certain preferred embodiments, the nano-fibrillated cellulose composition has the same thermal stability as that of the original lignocellulose material.

Embodiments of the invention are described in this summary, and in the Detailed Description of the Invention, below, which is incorporated here by reference. Although the invention has been described in connection with specific embodiments, it should be understood that the invention as claimed should not be unduly limited to such specific embodiments.

DEFINITIONS

Figure 1:
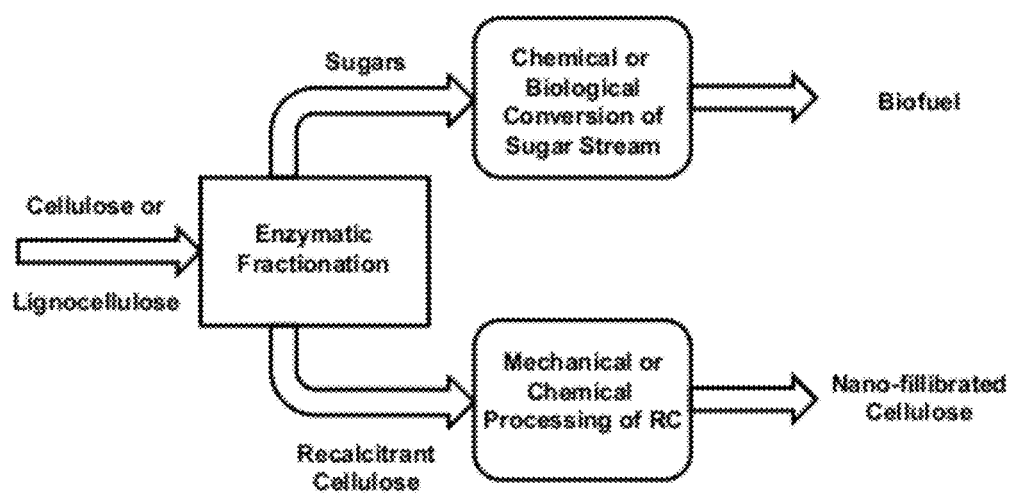
FIG. 1 shows a schematic of process diagram of the present invention.

To facilitate understanding of the invention, a number of terms are defined below.

As used herein, the term "saccharide" refers to a sugar, such as a monosaccharide, a disaccharide, an oligosaccharide or a polysaccharide. Monosaccharides include, but are not limited to, glucose, xylose, mannose, arabinose, galactose, and fructose. Disaccharides include, but are not limited to, sucrose and lactose. Polysaccharides include, but are not limited to, cellulose, hemicellulose and lignocellulose or starch.

As used herein, the term "cellulose" refers to a homopolymer of β(1→4) linked D-glucose units that form a linear chain. Cellulose can contain several hundred to several thousand or more glucose units, making cellulose a polysaccharide. Cellulose is found in many natural products, such as the cell walls of plants, and thus can be found in wood, pulp and cotton, among others.

As used herein, the term "hemicellulose" refers to a heteropolymer containing different saccharide units, such as, but not limited to, xylose, mannose, galactose, rhamnose and arabinose. Hemicellulose forms a branched polymer with several hundred to several thousand sugar units. Hemicellulose can include both pentose and hexose sugars.

As used herein, the term "enzyme" refers to a natural, bioengineered, or synthetic polypeptide or group of polypeptides that catalyzes a chemical or biochemical reaction, such as the synthesis or hydrolysis of cellulose.

As used herein the term "cellulase" refers to enzymes that hydrolyze cellulose.

As used herein the term "hemicellulase" is a collective term for the groups of enzymes that hydrolyze hemicelluloses, such as xylanase.

As used herein, the term "lignocellulose" or "lignocellulosic material," or similar terms, refers to natural and/or synthetic materials containing cellulose and/or hemicellulose. Generally, these materials also contain (but need not contain) lignin, xylan, protein, and/or other carbohydrates, such as starch. Lignocellulosic material is found, for example, in the stems, leaves, hulls, husks, and cobs of plants or leaves, branches, and wood of trees. Lignocellulosic material can include virgin plant biomass and/or non-virgin plant biomass such as agricultural biomass, commercial organics, construction and demolition debris, municipal solid waste, waste paper, and yard waste. Common forms of lignocellulosic material include trees, shrubs, grasses, wheat, wheat straw, sugar cane bagasse, corn, corn husks, corn kernel including fiber from kernels, products and by-products from milling of grains such as corn, rice, wheat, and barley (including wet milling and dry milling), as well as municipal solid waste, waste paper, and yard waste. The lignocellulosic material can also be, but is not limited to, herbaceous material, agricultural residues, forestry residues, and paper mill residues. Additional examples include but are not limited to branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet pulp, wheat midlings, oat hulls, hard and soft woods, organic waste materials generated from agricultural processes including farming and forestry activities, specifically including forestry wood waste, or a mixture thereof. In some embodiments, the lignocellulosic material is eucalyptus pulp. In some embodiments, the lignocellulosic material is wood fiber. Lignocellulosic material may comprise bleached materials, such as bleached pulp, or unbleached materials. Methods for preparing lignocellulosic material to produce, e.g., pulp, for use in the methods and systems of the present invention are common in the art. Numerous technologies have been developed, implemented, and improved over the last century in modern pulp and paper production. Currently, there are several main pulp production processes: (1) kraft pulping uses sodium hydroxide and sodium sulfide to produce both unbleached and bleached pulps (after subsequent bleaching); (2) soda pulping uses sodium hydroxide to produce bleached and unbleached pulps mainly from non-woody biomass; (3) mechanical pulping uses mechanical disk refining to produce newsprint-grade pulps, (4) chemical-mechanical pulping uses chemicals, such as sulfite and hydrogen peroxide, to pre-treat wood chips prior to disk refining to produce pulps for certain grade applications, such as boxes; and (5) sulfite pulping, including acidic to alkaline sulfite pulping, produces dissolved pulp. Neutral sulfite pulping (a special chemical-mechanical pulp, NSSC) uses sulfite with a base. Detailed description of different pulping processes can be found, e.g., in two series books: (I) "Pulp and Paper Manufacture", Vol. 1-10, 3rd ed., 1985, Ed: the Joint text book committee of the paper industry, TAPPI, ISBN: 0-919893-04-X, and (II) "Papermaking Science and Technology", Eds: Gullichsen and Paulapuro, Vol 1-19, Fapet Oy, 2000, ISBN: 952-5216-00-4.

In some embodiments, the lignocellulosic material is chemically and or mechanically pretreated woody or non-woody materials. The pretreatment was for subsequent enzymatic saccharification for sugar production. A variety of chemical and mechanical pretreatment methods are contemplated, including but not limited to, dilute acid, hot-water, ammonia, alkali, SPORL, steam explosion, ionic liquid, organosolv, etc., which have been well described in the literature (see, e.g. Zhu and Pan (2010), *Bioresource Technology*, 101: 4992-5002; Hendriks and Zeeman (2009), *Bioresource Technology*, 100:10-18, both herein incorporated by reference in their entireties for all purposes.)

As used herein, the term "cellulosic ethanol," "cellulosic biofuel," or similar terms, refers to a biofuel produced from wood, grasses, or the non-edible parts of plants. More specifically, it is a type of biofuel produced from lignocellulose or lignocellulosic materials.

As used herein, "plant biomass" refers to biomass that includes a plurality of components found in plants, such as lignin, cellulose, hemicellulose, beta-glucans, homogalacturonans, and rhamnogalacturonans.

As used herein, the term "recalcitrant cellulose" refers to the resultant solids from enzyme pretreatment that consists of mainly cellulose may contain lignin and or hemicelluloses such as xylan. Recalcitrant cellulose is difficult to hydrolyze to glucose, and is usually more crystalline than cellulose that is more readily hydrolyzed, a feature that imparts a high degree of structural integrity and mechanical strength to cellulose and renders it recalcitrant towards hydrolysis aimed at producing, e.g., fermentable sugars. In general, neither water molecules nor catalysts for hydrolysis (saccharification) are able to easily penetrate the crystalline matrix.

As used herein, the terms "nanocellulose" and "nanofibrillated cellulose" and "cellulose nanofibers" are used interchangeably to refer to cellulose polymeric fibers or fibrous networks exhibiting some degree of crystallinity, e.g., as measurable by Raman spectroscopy or x-ray diffraction. Nanocellulose is not limited to a particular size, but preferably has fibers or fibrous segments with diameters of on the order or 1 µm or less, preferably less than about 500 nm, more preferably between about 10 nm and 300 nm. In certain preferred embodiments, the nano-cellulose has fibers or fibrous segments with diameters averaging about 20 nm and lengths averaging approximately 500 nm to 1 µm.

As used herein, the terms "microcellulose" and "microfibrillated cellulose" and "cellulose microfibers" are used interchangeably to refer to cellulose polymeric fibers or fibrous networks exhibiting some degree of crystallinity, e.g., as measurable by Raman spectroscopy or x-ray diffraction, and having fibers or fibrous segments with diameters of on the order or 1 µm or more.

As used herein, the term "biofuel" refers to any fuel that is derived from a biomass, i.e., recently living organisms, e.g., plants, or their metabolic byproducts, such as manure from cows. It is a renewable energy source, unlike other natural resources such as petroleum, coal and nuclear fuels.

"Fuel" refers to one or more hydrocarbons, one or more alcohols, one or more fatty esters or a mixture thereof. Preferably, liquid hydrocarbons are used. Fuel can be used to power internal combustion engines such as reciprocating engines (e.g., gasoline engines and diesel engines), Wankel engines, jet engines, some rocket engines, missile engines and gas turbine engines. In some embodiments, fuel typically comprises a mixture of hydrocarbons such as alkanes, cycloalkanes and aromatic hydrocarbons. In other embodiments, fuel comprises limonane.

"Jet fuel" refers to a fuel suitable for use in a jet engine.

"Chemcials" as used in reference to compositions produced from lignocellulosic material refers to one or more chemical compositions derived from a hydrolyzed sugar fraction through a variety of pathways, such as chemical or enzymatic methods.

DETAILED DESCRIPTION OF THE INVENTION

The present invention provides an integrated process for the simultaneous production of fermentable sugars (e.g., for biofuel or chemical production) and nano-cellulose (a potentially valuable biobased nanomaterial for commercial applications) from plant biomass. The integrated process uses an environmentally friendly enzyme treatment of cellulosic/lignocellulosic material to hydrolyze amorphous cellulose and hemicelluloses to sugars that can be converted to biofuels, and to produce recalcitrant crystalline cellulose for further chemical and/or mechanical processing to produce nano-fibrillated cellulose. The method significantly reduces the cost of producing biofuels by avoiding the need for complete cellulose saccharification, thus reducing reaction times and/or avoiding the use of harsh conditions typically needed to achieve maximum hydrolysis of cellulose. The enzyme pretreatment also reduces the amount of energy necessary for mechanical processing recalcitrant cellulose to produce nano-fibrillated cellulose. Although the invention is described in conjunction with the production of nanocellulose, it is understood that the methods and systems of the present invention are applicable to the production of fibers of any size, e.g., micro-fibrillated cellulose.

The production of cellulosic biofuels can mitigate climate change through the reduction of greenhouse gas emissions for sustainable economic development (see, e.g., Farrell A E, et al. (2006) *Science* 311(5760):506-508; Scharlemann J P W & Laurance W F (2008) *Science* 319:43-44; each herein incorporated by reference in their entireties). However, cellulosic biofuel production is not economical using current technologies (see, e.g., Aden A, et al. (2002) Lignocellulosic biomass to ethanol process design and economics utilizing co-current dilute acid prehydrolysis and enzymatic hydrolysis for corn stover. NREL/TP-510-32438; herein incorporated by reference in its entirety). One of the key technical barriers to economical cellulosic biofuel production through biochemical conversion is the high cost and low efficiency of enzymatic cellulose saccharification of lignocellulosic biomass due to its strong recalcitrance (see, e.g., Himmel M E, et al. (2007) *Science* 315(5813):804-807; Zhu J Y, Pan X J, & Zalesny Jr. R S (2010) Applied Microbiology and Biotechnology 87: 847-857; each herein incorporated by reference in their entireties). It is very difficult to achieve near complete cellulose saccharification even with good pretreatment (described in the previous section) and at high cellulase loadings after a long period of hydrolysis. This is especially true, for example, when saccharification is conducted under high cellulosic solids consistencies required to achieve high biofuel titer to reduce distillation/separation energy consumption (see, e.g., Zhang X, Qin W, Paice M G, & Saddler J N (2009) Bioresource Technology 100:5890-5897; herein incorporated by reference in its entirety). Previous research efforts in cellulosic biofuels have focused on overcoming the recalcitrance of lignocelluloses to enhance the saccharification of the recalcitrant cellulose (see, e.g. Zhang Y H P & Lynd L R (2004) Biotechnology and Bioengineering 88(7):797-824; herein incorporated by reference in its entirety).

Cellulose as a structural material is extremely strong with a theoretical modulus of around 250 GPa (see, e.g., Wegner T H & Jones E P (2009). A fundamental review of the relationships between nanotechnology and lignocellulosic biomass is illustrated in Nanoscience and Technology of Renewable Biomaterials, eds Lucia L A & Rojas O J (John Wiley and Sons), 1st Ed, pp 1-41; herein incorporated by reference in its entirety) or a specific tensile strength of about 5200 kN.m/kg or about 18 times that of titanium. However, most cellulose is naturally present in plant lignocellulosic biomass as a biocomposite made of cellulose, hemicelluloses, lignin, etc., with a hierarchical structure (see, e.g., Wegner T H & Jones E P (2009). A fundamental review of the relationships between nanotechnology and lignocellulosic biomass is discussed in The Nanoscience and Technology of Renewable Biomaterials, eds Lucia L A & Rojas O J (John Wiley and Sons), 1st Ed, pp 1-41; herein incorporated by reference in its entirety). Advanced separation techniques have been used to effectively liberate cellulose from lignocellulosic biomass in the forms of elementary fibrils and nanofibrils made of elementary fibrils.

There are several approaches for nanocellulose production from plant biomass. Acid hydrolysis was developed in the 1940s (see, e.g., Nickerson R F & Habrle J A (1947) Ind. Eng. Chem. 39:1507-1512; herein incorporated by reference in its entirety) and remains a major process to produce stable colloidal suspensions of cellulose nanocrystals (CNC) (see, e.g., Bondeson D, A. M, & Oksman K (2006) Cellulose 13:171-180; Chen Y, Liu C, Chang P R, Cao X, & Anderson D P (2009) Carbohydrate Polymers 76(4):607-615; Moran J L, Alvarez V A, Cyras V P, & Vazquez A (2008) Cellulose 15:149-159; Favier V, Chanzy H, & Cavaille J Y (1995) Macromolecules 28:6365-6367; Marchessault R H, Morehead F F, & Koch M J (1961) J. Colloid Sci. 16:327-344; Dong X M, Revol J F, & Gray D G (1998) Cellulose 5:19-32; each herein incorporated by reference in their entireties). The process for creating CNC has a very low yield of about 30-40% (see, e.g., Bondeson D, A. M, & Oksman K (2006) Cellulose 13:171-180; herein incorporated by reference in its entirety). The usage of strong sulfuric acid is a hazard and also is an environmental concern for waste stream treatment. Furthermore, hydrolyzed celluloses and hemicelluloses (about 60 to 70%) that are dissolved in 64% sulfuric acid would be difficult to recover for biofuel production.

Mechanical homogenization or shearing has also been used to produce nano-fibrillated cellulose (NFC) (see, e.g., Nakagaito A N & Yano H (2004) Applied Physics A: Materials Science and Processing 78:547-552; Iwamoto S, Nakagaito A N, & Yano H (2007) Applied Physics A: Materials Science and Processing 89:461-466; Alemdar A & Sain M (2008) Bioresource Technology 99:1664-1671; Andresen M, Johansson L-S, Tanem B S, & Stenius P (2006) Cellulose 13:665-677; each herein incorporated by reference in their entireties). However, mechanical homogenization or shearing used to produce nano-fibrillated cellulose is very energy intensive. For example, energy consumption can be 20,000-30,000 kWh/ton or 72-108 GJ/ton (see, e.g., Siró I & Plackett D (2010) Cellulose 17(3):459-494; herein incorporated by reference in its entirety) or about 4-5 times the energy stored in wood.

Chemical pretreatments (e.g., alkaline pretreatment (see, e.g., Wang B, Sain M, & Oksman K (2007) Applied Composite Materials 14:89-103; Dufresne A, Cavaillé J-Y, & Vignon M R (1997) J. Appl Polym Sci 64:1185-1194; each herein incorporated by reference in their entireties)) can significantly reduce this energy consumption (see, e.g., Pääkko M, et al. (2007) Biomacromolecules 8:1934-1941; herein incorporated by reference in its entirety). For example, the 2,2,6,6-tetramethylpiperidine-1-oxyl radical (TEMPO)-mediated oxidation of cellulose fibers achieved some level of success in efficiently producing NFC (see, e.g., Saito T, Kimura S, Nishiyama Y, & Isogai A (2007) Biomacromolecules 8:2485-2491; Saito T & Isogai A (2004) Biomacromolecules 5:1983-1989; Saito Ta, Okita Y, Nge T T, Sugiyama J, & Isogai A (2006) Carbohydrate Polymers 65:435-440; Okita Y, Saito T, & Isogai A (2009) Holzforschung 63:529-535; each herein incorporated by reference in their entireties). However, TEMPO is a very expensive chemical, and effective methods for the recovery of TEMPO need to be developed.

Enzyme pretreatment is an alternative to chemical pretreatment for nanocellulose production by mechanical homogenization (see, e.g., Pääkko M, et al. (2007) Biomacromolecules 8:1934-1941; Henriksson M, Henriksson G, Berglund L A, & Lindström T (2007) European Polymer Journal 43(8):3434-3441; Hayashi N, Kondo T, & Ishihara M (2005) Carbohydrate Polymers 61:191-197; each herein incorporated by reference in their entireties). For example, both commercial endoglucanase (see, e.g., Pääkko M, et al. (2007) Biomacromolecules 8:1934-1941; Henriksson M, Henriksson G, Berglund L A, & Lindström T (2007) European Polymer Journal 43(8):3434-3441; each herein incorporated by reference in their entireties), such as Novozyme 476, and purified exoglucanase from commercial cellulose (see, e.g., Henriksson M, Berglund L A, Isaksson P, Lindström T, & Nishino T D (2008) Biomacromolecules 9:1579-1585; herein incorporated by reference in its entirety) have been used. However, these studies focused on high-yield production of nanocellulose. Hydrolyzed sugars were not recovered, analyzed or utilized.

Such problems associated with cellulosic biofuel production and nanocellulose production from lignocellulosic material are addressed and overcome with the compositions, systems and methods of the present invention. In particular, the present invention provides novel fractionation processes configured to integrate production of usable hydrolyzed sugars (e.g., for biofuel production) and recalcitrant cellulose (e.g., for nano-fibrillated cellulose production) from lignocellulosic material, and methods of using the same (e.g., in the production of biofuel and nano-fibrillated cellulose). Indeed, experiments conducted during the course of developing embodiments for the present invention demonstrated the feasibility of integrating the productions of biofuel and nano-fibrillated cellulose from lignocellulosic material (e.g., wood fibers, pretreated plant biomass substrates).

Accordingly, the present invention relates to systems, compositions and methods for the conversion of lignocellulosic material to recalcitrant cellulose and hydrolyzed sugars and products produced therefrom (e.g., biofuel, nano-fibrillated cellulose and nano-cellulose products). In particular, the invention provides novel fractionation processes configured to integrate production of hydrolyzed sugars (e.g., for biofuel production) and recalcitrant cellulose from lignocellulosic material and methods of using the same.

The present invention is not limited to a particular type of lignocellulosic material. In some embodiments, the lignocellulosic material is a natural material. Natural lignocellulosic materials include but are not limited to materials containing cellulose and/or hemicellulose. Generally, these materials also contain lignin, xylan, protein, and other carbohydrates, such as starch. Lignocellulosic material is found, for example, in the stems, leaves, hulls, husks, and cobs of plants or leaves, branches, and wood of trees. Lignocellulosic material can include virgin plant biomass and/or non-virgin plant biomass such as agricultural biomass, commercial organics, construction and demolition debris, municipal solid waste, waste paper, paper mill sludge, farm animal waste (e.g., partially digested grasses from cows) and yard waste, etc. Lignocellulosic material may be chemically or mechanically pretreated using, e.g., hot water, dilute acid, alkaline solutions, etc. to facilitate enzyme fractionation or saccharification as described in the previous section, or may be used without further chemical or mechanical pretreatment or processing.

The present invention is not limited to particular fractionation processes configured to integrate production of hydrolyzed sugars (e.g., for biofuel production) and recalcitrant cellulose (e.g., for nano-fibrillated cellulose production) from lignocellulosic material. In some embodiments, the fractionation processes involve application of an enzyme pretreatment to cellulosic/lignocellulosic substrate so as to hydrolyze the amorphous cellulose and/or hemicelluloses to sugars (e.g., for biofuel production) and generate recalcitrant cellulose (e.g., for nano-fibrillated cellulose production).

Experiments conducted during the course of developing embodiments for the present invention determined that crystalline cellulose is much more recalcitrant and remained as solid after enzymatic pretreatment and can be used, for example, to produce nano-fibrillated cellulose through mechanical or chemical processing. In addition, it was determined that the hydrolyzed sugars can be converted to biofuel or biofuel intermediates through chemical catalysis, enzyme synthesis, or fermentations, etc. It was determined that such an enzyme pretreatment significantly reduced energy consumption for producing nano-fibrillated cellulose by mechanical processing, such as high shear homogenization.

The present invention is not limited to a particular enzyme pretreatment for use in the novel fractionation processes configured to integrate production of hydrolyzed sugars (e.g., for biofuel production) and recalcitrant cellulose (e.g., for nanocellulose production) from lignocelluloses. In some embodiments, the enzyme pretreatment includes use of compositions having one or more of cellulase, xylanase, endoxylanase, exoxylanase, beta xylosidase, endomannase, beta-mannosidase, beta-mannase, pectin lyase, pectate lyase, endopolygalacturonase, exopolygalacturonase, rhamnohydrolase, xylogalacturonase, alpha-rhamnosidase, rhamnogalacturonan lyase, xylosidase, arabinofuranosidase, arabinofuranohydrolase, endoarabinase, exoarabinase, endogalactanase, glucuronidase, feruloyl esterase, p-coumaroyl esterase, galactosidase, endoglucanase, exoglucanase, protease, lipase, glucoamylase, cellobiohydrolase, alpha amylase, acetyl esterase, methyl esterase, lignin peroxidase, and/or laccase. In some embodiments the enzyme pretreatment includes use of compositions comprising one or more commercial cellulase enzymes, or specially formulated enzymes for effective fractionation of recalcitrance cellulose (RC). Examples of such commercial cellulase enzymes include, but are not limited to, endoglucanase (e.g., Novozyme 476), complex cellulase of Genencor Multifect B, and exoglucanase.

The present invention is not limited to a particular fractionation process technique designed to integrate production of hydrolyzed sugars (e.g., for biofuel production) and recalcitrant cellulose (e.g., for nano-fibrillated cellulose production)

from lignocellulosic material through application of an enzyme pretreatment to the cellulosic/lignocellulosic substrate. In some embodiments the enzyme pretreatment involves contacting (e.g., incubating; mixing) lignocellulosic material with compositions comprising one or more enzymes (e.g., cellulase enzymes). Any ratio of lignocellulosic material to enzyme is permissible. For example, in some embodiments, the ratio of lignocellulosic material to enzyme is approximately 10 grams lignocellulosic material to 1-100 filter paper units (FPU) of enzyme or 1 kg lignocellulosic material to 1000-10,000 FPU enzymes, but one of skill in the art might use, e.g., 1, 2, 3, 4, 5, 6, 7, 8, 9, 10, 11, 12, . . . 90, 91, 92, 93, 94, 95, 96, 97, 98, 99 or more FPU per gram of lignocellulosic material, or fractional amounts thereof. The fractionation process techniques are not limited to a particular time duration having the lignocellulosic material contact (e.g., incubate, mix) with the compositions comprising one or more enzymes (e.g., cellulase, hemicellulase enzymes). In some embodiments, the hydrolysis step of the fractionation process are not limited to a particular time duration, while in some embodiments, the duration of the fractionation process techniques is from approximately 1 hour (e.g., 20 minutes, 30 minutes, 45 minutes, 1 hour, 70 minutes, 80 minutes, 90 minutes, etc.) to approximately 72 hours (e.g., 50 hours, 60 hours, 68 hours, 70 hours, 72 hours, 75 hours, 80 hours, etc.). The hydrolysis process techniques are not limited to particular pH and temperature ranges. In some embodiments, enzymatic hydrolysis can be conducted in a range of pH and temperature depending on the enzymes used. For example, a pH range from 3 to 9 and a temperature range from 25 to 80° C. can be used for most commercial enzymes (e.g., endoglucanase (e.g., Novozyme 476), complex cellulase of Genencor Multifect B, and exoglucanase). In some embodiments, the pH range is from 4.5 to 7.5 and the temperature range from 35 to 50° C. The hydrolysis process techniques are not limited to a particular manner of separating the liquid and solid fractions. In some embodiments, the liquid and solid fractions are separated through filtration, e.g., with a filter paper or a screen.

The present invention is not limited to a particular manner of converting recalcitrant cellulose to nano-fibrillated cellulose (see, e.g., U.S. Patent Application Publication Nos. 2010/0003519, 2007/0152378; each herein incorporated by reference in their entireties). In some embodiments, recalcitrant cellulose is converted to nano-fibrillated cellulose through chemical processing. In some embodiments, recalcitrant cellulose is converted to nano-fibrillated cellulose through mechanical processing (e.g., mechanical homogenization). In some embodiments, the recalcitrant cellulose is diluted (e.g., diluted to approximately 0.3% w/v) (e.g., diluted with deionized water) prior to homogenization (e.g., with a blender) (e.g., with a microfluidizer).

The present invention is not limited to a particular manner of converting hydrolyzed sugar to biofuel (see, e.g., U.S. Pat. Nos. 7,754,456, 7,514,247, 5,916,780, and 4,650,689, and U.S. Patent Application Publication Nos. 2010/0146842, 2009/0325252, 2009/0288788, 2009/0156868, 2008/0044877, 2006/0177917, 2006/0014260, and 2003/0054500; each herein incorporated by reference in their entireties). In some embodiments, conversion of hydrolyzed sugar to biofuel (e.g., ethanol) is accomplished through chemical catalysis, enzyme synthesis, or fermentation techniques (e.g., yeast fermentation).

EXPERIMENTAL

The following examples are provided in order to demonstrate and further illustrate certain embodiments and aspects of the present invention and are not to be construed as limiting the scope thereof.

Example 1

Production of Hydrolyzed Sugar and Recalcitrant Cellulose Fractions, and Products Thereof from Lignocellulosic Material Materials and Methods Materials:

A wet bleached Kraft eucalyptus pulp was used as received. The pulp was frozen in a freezer at −4° C. before use. The major chemical components of the pulp were: glucan=92.9%, xylan=5.7%, Klason lignin=1.2%. Endoglucanase of Novozyme 476 (Novozymes, Franklinton, N.C.) and complex cellulase of Genencor Multifect B (Genencor, Palo Alto, Calif.) was used as received.

Enzymatic Hydrolysis:

Enzymatic hydrolysis of the eucalyptus pulp was conducted in a 250 mL flask on shaking bed (Thermo Fisher Scientific, Model 4450, Waltham, Mass.) at 10% (w/V) solids consistency, i.e., 10 g of pulp in 100 mL cellulase solutions. The loadings of cellulases of Novozym 476 and Genencor multifect B were 10 and 5 FPU/g substrate, respectively. Hydrolysis experiments were all conducted at 50° C. and buffered at pH 4.8 using sodium acetate but with varied durations from 1-72 hours. At the end of each experiment, the solid/liquid sample was separated by filtration through a filter paper (Sartonlon Polymid, pore size 0.45 μm, Sartorius Stedim Biotech GmbH, Goettingen, Germany). The liquid sample produced from the 72 hours hydrolysis was stored in a freezer at −16° C. for subsequent fermentation to ethanol.

Determination of Degree of Polymerization and Crystallinity of Fractionated Solids:

The degrees of polymerization (DP) of the cellulase fractionated cellulosic solids were measured according to TAPPI Standard Test Method T230 om-99 (see, e.g., TAPPI (2009) TAPPI Test Methods (Technical Association of the Pulp and Paper Industry, Atlanta, Ga.); herein incorporated by reference in its entirety). 0.1 g of oven-dried cellulosic solids was first dissolved into 20 mL of a 0.25M cupriethylenediamine a solution. The viscosity of the resultant solution was determined by a capillary viscometer. The DP of the cellulose was calculated using the following expression (see, e.g., Mazumder B B, Ohtani Y, Cheng Z, & Sameshima K (2000) Journal of Wood Science 46:364-370; herein incorporated by reference in its entirety):

$$DP^{0.905} = 0.75[954 \log(X) - 325] \quad (1)$$

where X is the measured viscosity.

The crystallinities of these residual solids were measured by a FT-Raman spectroscopic method (see, e.g., Agarwal U P, Reiner R S, & Ralph S A (2010) Cellulose 17(4):721-733; herein incorporated by reference in its entirety). Approximately 0.25 g of air-dried sample was pressed into a pellet that was analyzed using a Bruker RFS 1000 spectrometer (Bruker Instruments Inc., Billerica, Mass.). The sample crystallinity index was calculated using the Raman scattering intensities at two wavenumbers ($cm^{-1}$) as follows:

$$Cr_{Raman} = \frac{\left(\frac{I_{380}}{I_{1,096}}\right) - 0.0286}{0.0065} \quad (2)$$

Nano-Fibrillated Cellulose (NFC) Production:

The recalcitrant cellulosic (RC) solids collected at the end of 48 h hydrolysis was used for NFC production through mechanical homogenization. The recalcitrant cellulose from enzymatic hydrolysis was diluted to approximately 0.3% (w/V) in deionized water, and mixed in a household Waring blender for minutes. A Microfluidizer processor (M-110EH-30 Microfluidics, Newton, Mass.) was used to homogenize the recalcitrant cellulose into NFC. The 0.3% suspension was passed through the Microfluidizer up to 50 times using a 200 micron chamber and 10 additional times using an 87 micron chamber to produce highly nano-fibrillated cellulose. The homogenized cellulosic fibers were collected and characterized after 10, 20, 50 and 60 total passes.

Electron Microscopy:

Specimens for scanning electron microscopy (SEM) were prepared by drying drops of the aqueous slurry on aluminum mounts. All SEM specimens were sputter coated with gold to provide adequate conductivity for examination in a Zeiss EVO 40 SEM under ultrahigh vacuum conditions. For transmission electron microscopy (TEM), aqueous NFC suspensions (0.2%, w/V) were further diluted in water by a factor of 300 and sonicated. Drops of approximately 2-3 microliters were deposited and dried on TEM sample grids containing ultrathin carbon films of about 3 nm in thickness supported by thicker carbon films with holes. A Philips CM120 transmission electron microscope with an accelerating potential of 80 keV was used to image these fibers.

Production and Testing of NFC Films:

Films of fibers resulted from various degrees of mechanical homogenization were formed by ultrafiltration of fiber slurries using a 142 mm Millipore ultrafiltration apparatus with polytetrafluoroethylene (PTFE) membranes with 0.1 micrometer pore sizes (Millipore JVWP14225, Bedford, Mass.). Filter paper was placed below the ultrafiltration membranes to provide support. Fiber slurries of approximately 0.2% (w/V) were added to the ultrafiltration apparatus to make sheets with a target weight of 1.0 g. After dewatering, individual films were blotted and placed between filter and blotter papers. The films and filter papers were placed between smooth metal caul plates and allowed to dry at room temperature under a pressure of approximately 14–20 kPa for three days.

The mechanical and optical properties of the films were measured according to TAPPI Standard Test Methods (see, e.g., TAPPI (2009) TAPPI Test Methods (Technical Association of the Pulp and Paper Industry, Atlanta, Ga.); herein incorporated by reference in its entirety). The films were first conditioned according to TAPPI Method T 402, i.e., preconditioning at 22-40° C. under 10-35% relative humidity (RH) for at least 24 hours, followed by conditioning under 50±2.0% RH at 23±1.0° C. for at least 24 hours. Two sheets for each experimental condition were prepared and sampled for physical and mechanical testing. Three tensile specimens and eight zero-span specimens were obtained from each sheet. Tensile tests were performed based on TAPPI T 494 in which a span of 2.5 in, a width of 15 mm, and an elongation speed of 0.2 mm/min were used. Zero-span tensile tests were performed using a Zero Span Tensile (model ZST-15, Pulmac) according to TAPPI T 231 with sample specimens at least 20 mm wide. Reported zero-span tensile data was normalized to a basis weight of 60 g/m². The opacities of the films were performed according to TAPPI T 519.

Fermentation of Hydrolyzed Sugar:

Yeast Saccharomyces cerevisiae D5A (ATCC® Number: 200062) was used to ferment the enzyme-hydrolyzed sugars. To prepare seed culture, the strain was grown at 30° C. for 2 days on YPD-agar plates containing 10 g/L yeast extract, 20 g/L peptone, 20 g/L glucose, and 20 g/L agar. A colony of this strain was transferred from YPD-agar plates by loop to a fresh liquid YPD medium (10 g/L yeast extract, 20 g/L peptone, 30 g/L glucose) in a flask on a shaker (Thermo Fisher Scientific, Model 4450, Waltham, Mass.). The S. cerevisiae D5A seed culture was grown overnight at 35° C. with agitation at 90 rpm on a shaking bed before harvesting. The harvested culture was centrifuged at 5000 g for 5 min at 20° C. to yield cell pellets after decanting the supernatant. Cell concentration (dry cell weight per liter) was calculated based on 600 nm absorbance. An aliquot was transferred to hydrolysate for an initial cell concentration of 2 g dry cell weight per liter for fermentation. The sugar streams from cellulase hydrolysis were further hydrolyzed to glucose using β-glucosidase for ethanol production through fermentation. Fermentations were carried out in 250 mL Erlenmeyer flasks using the shaker/incubator at 35° C. and 90 rpm and buffered at pH 4.8. The open end of the flasks was wrapped with aluminum foil to prevent ethanol leak. No nutrients were added during fermentation. Samples from the fermentation broth were taken periodically for analysis. Reported results are the average of duplicate experiments.

Results

Enzymatic Hydrolysis of Amorphous and Crystalline Cellulose

Figure 2:
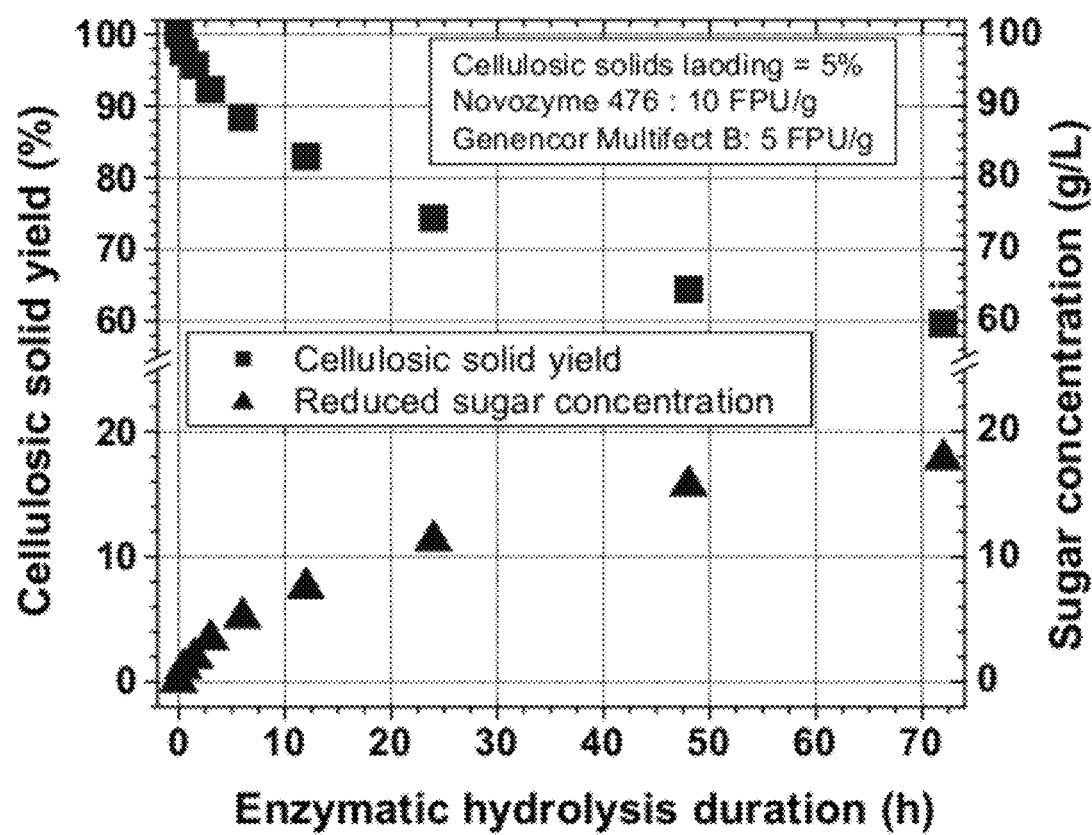
FIG. 2 shows the effect of enzymatic pretreatment duration on recalcitrant cellulose yield and reduced sugar concentration in the hydrolysate from a bleach eucalyptus pulp.
Figure 3:
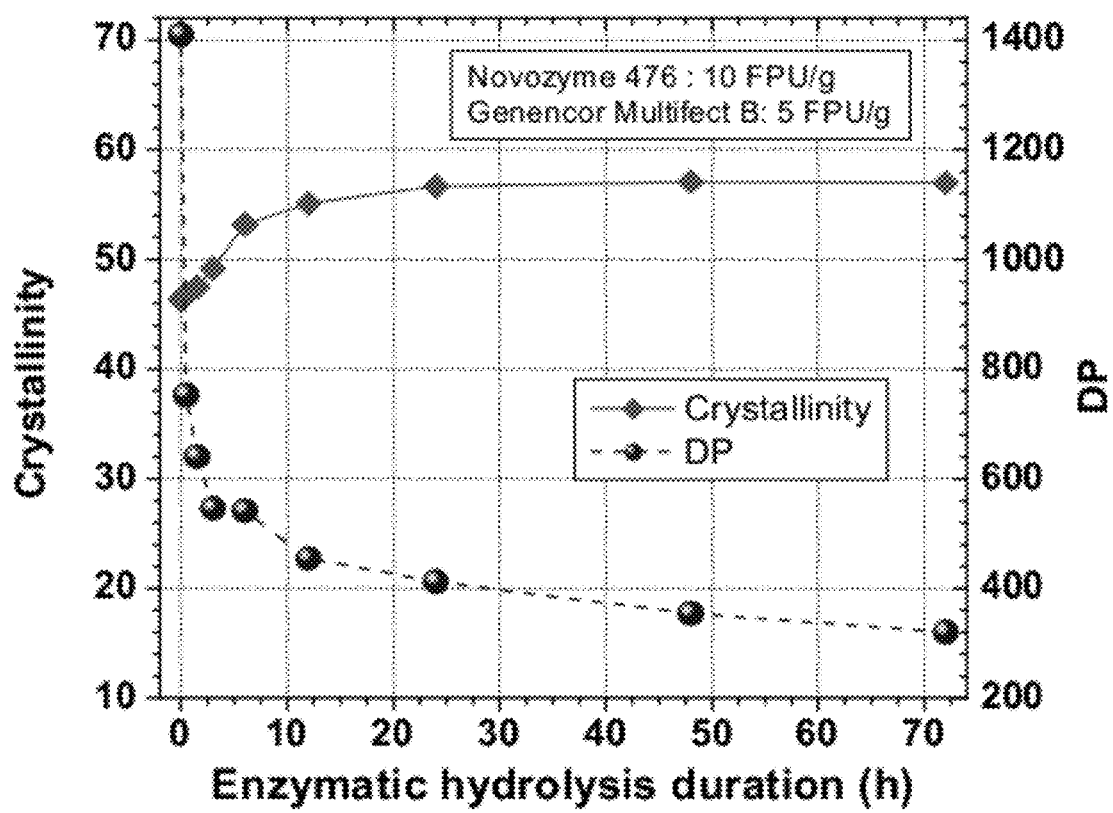
FIG. 3 shows the effect of enzymatic hydrolysis duration on DP and crystallinity of the resultant recalcitrant cellulose from a bleach eucalyptus pulp.
Figure 4:
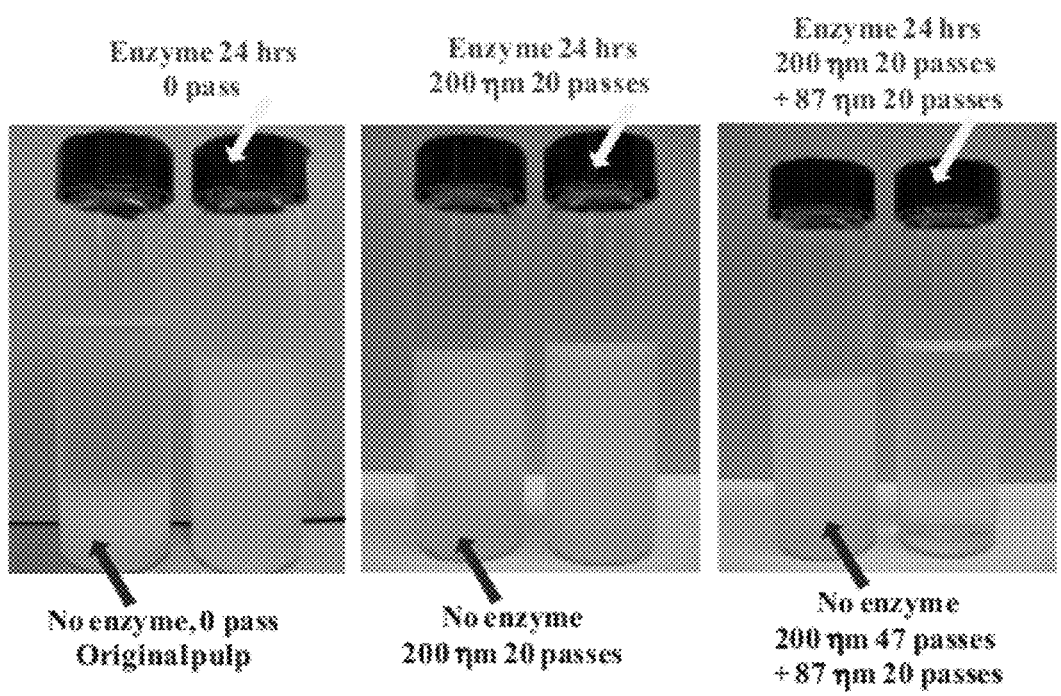
FIG. 4 shows images of cellulose suspension/solution under various degrees of homogenization, with comparisons between initial cellulose pulp with and without enzymatic fractionation.
Figure 5:
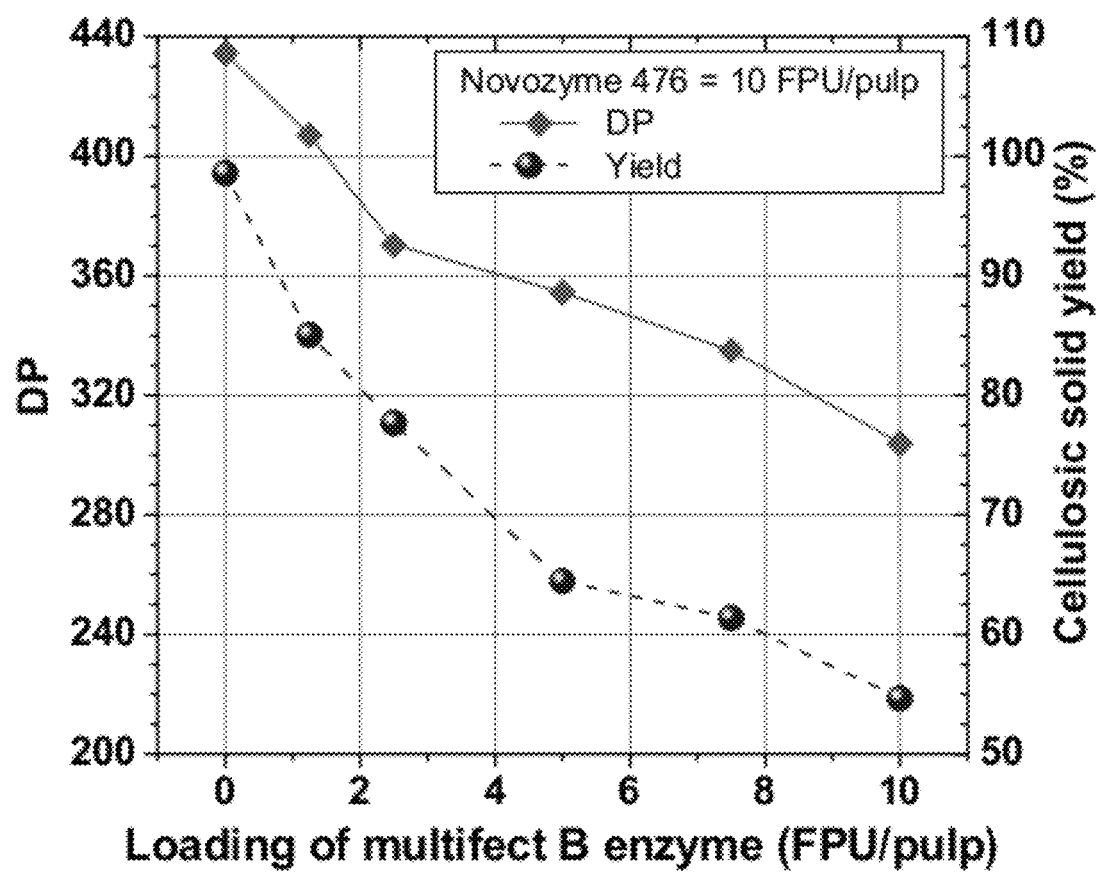
FIG. 5 shows the effect of multifect B enzyme loadings on cellulosic solid yield.

Effective hydrolysis of the amorphous segments from the crystalline segments of the wood pulp cellulose is critical to integrate the productions of NFC and sugar for cellulosic ethanol through fermentation. It was found that a range of desired yields of cellulosic solid substrate from 60-90% can be achieved by varying the enzymatic hydrolysis duration (FIG. 2). Similar degrees of enzymatic hydrolysis were also achieved by varying the loading of Multifect B cellulase. The cellulase also significantly reduced the degree of polymerization (DP) of the fractionated solid cellulose from 1400 to 400 after 48 hours hydrolysis (FIG. 3). Such hydrolysis is important to facilitate NFC production through mechanical means (see, e.g., Henriksson M, Berglund L A, Isaksson P, Lindström T, & Nishino T D (2008) Biomacromolecules 9:1579-1585; herein incorporated by reference in its entirety), as verified from images of the microfluidized suspensions. The suspension of the enzyme fractionated cellulosic solids after 60 passes of microfluidization (50 passes through a 200 μm nozzle and 10 additional passes through an 87 μm nozzle) was transparent, indicating the resultant cellulose is highly nanofibrillated. However, the suspension of the original bleached eucalyptus fibers remained opaque even after the more processing (FIG. 4). The measured crystallinity index of the fractionated recalcitrant cellulose was increased from 46 to 57 or increased by 24% after 48 hours hydrolysis. While not limited to a particular mechanism, these results indicate that the fractionated recalcitrant cellulosic solids contains primarily crystalline cellulose. Effective hydrolysis was also demonstrated by varying enzyme loadings (FIG. 5).

Figure 6:
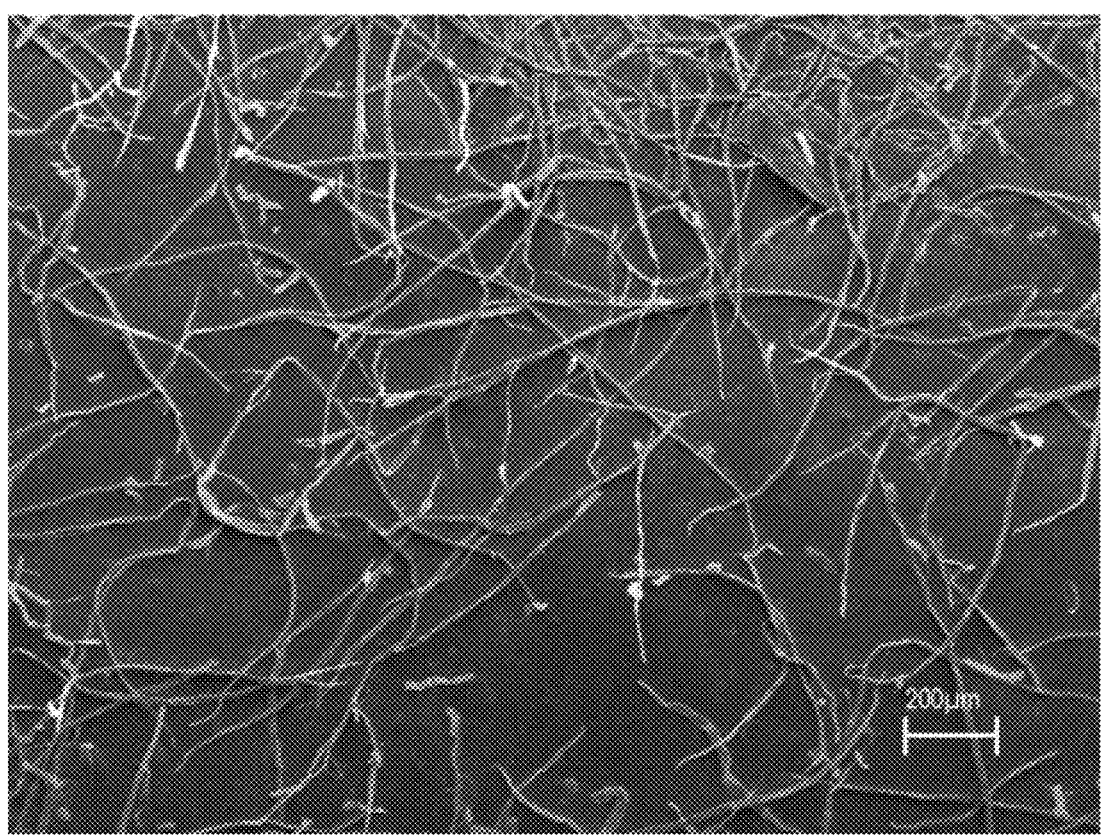
FIG. 6 shows an SEM image of original bleached eucalyptus wood fiber.
Figure 7A:
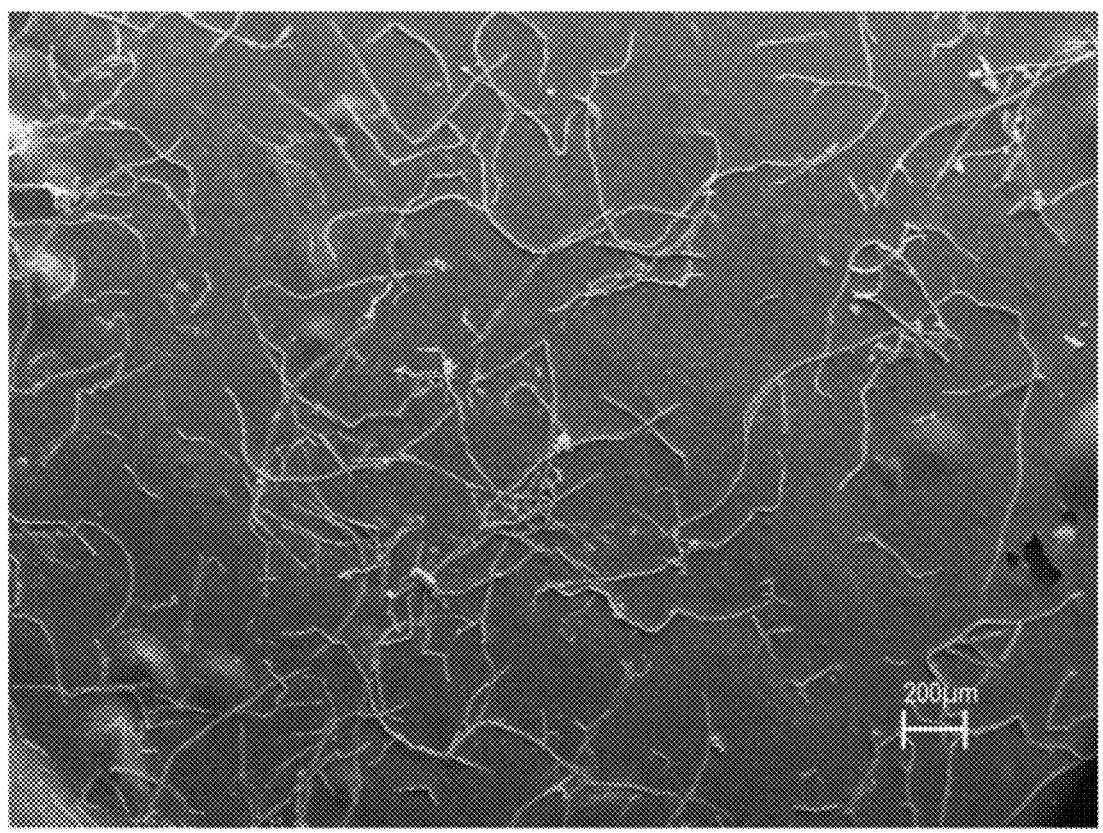
FIG. 7A-7C show SEM images of recalcitrant cellulose after 3, 12, and 24 hours, respectively, of enzymatic hydrolysis under enzyme loadings of 5 FPU Genencor Multifect B+5 FPU Novozyme 476.
Figure 7B:
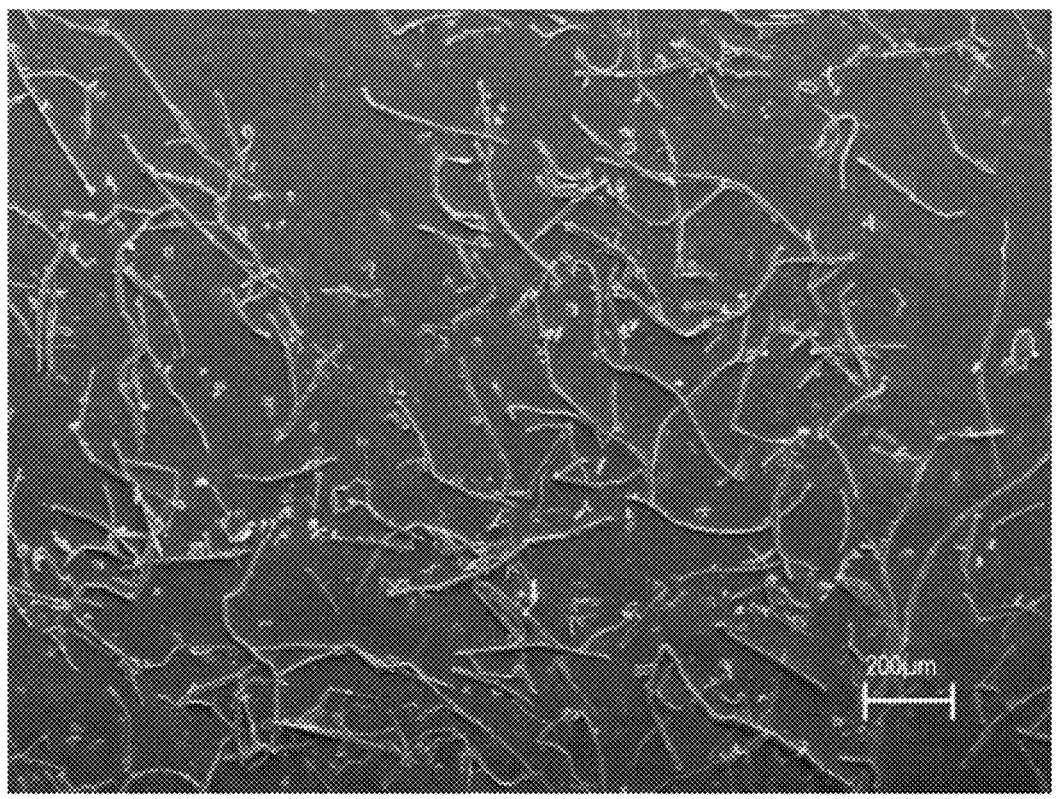
Figure 7C:
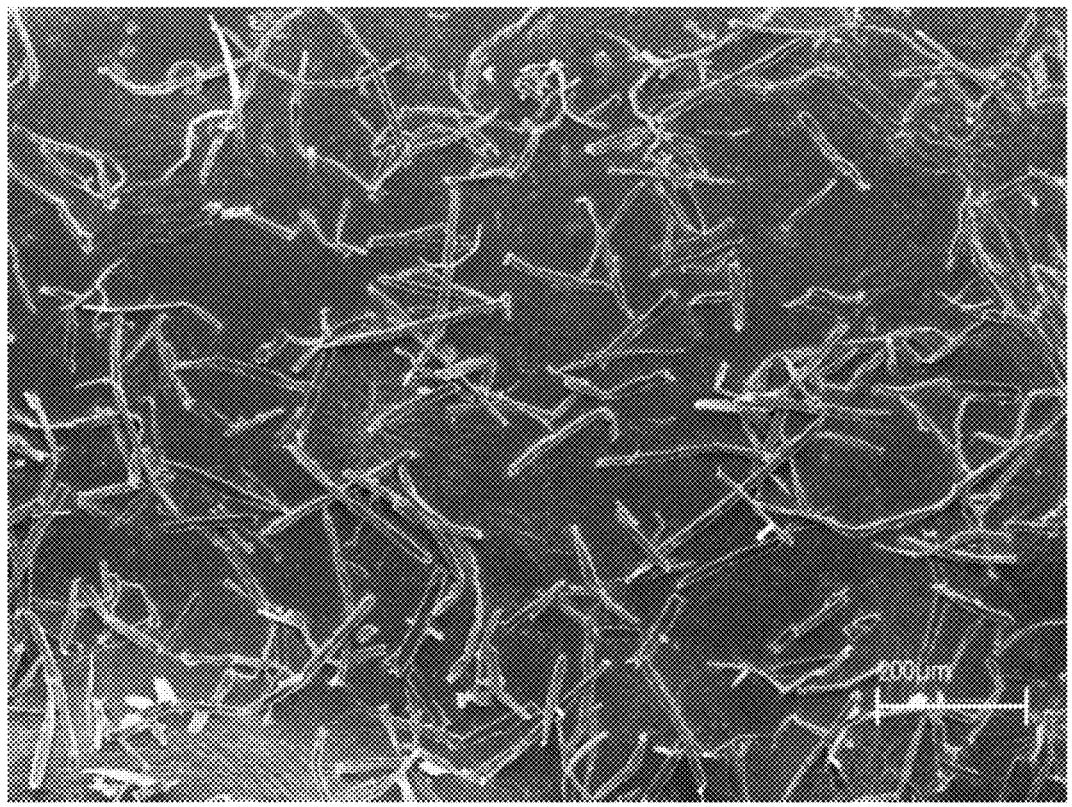
Figure 8A:
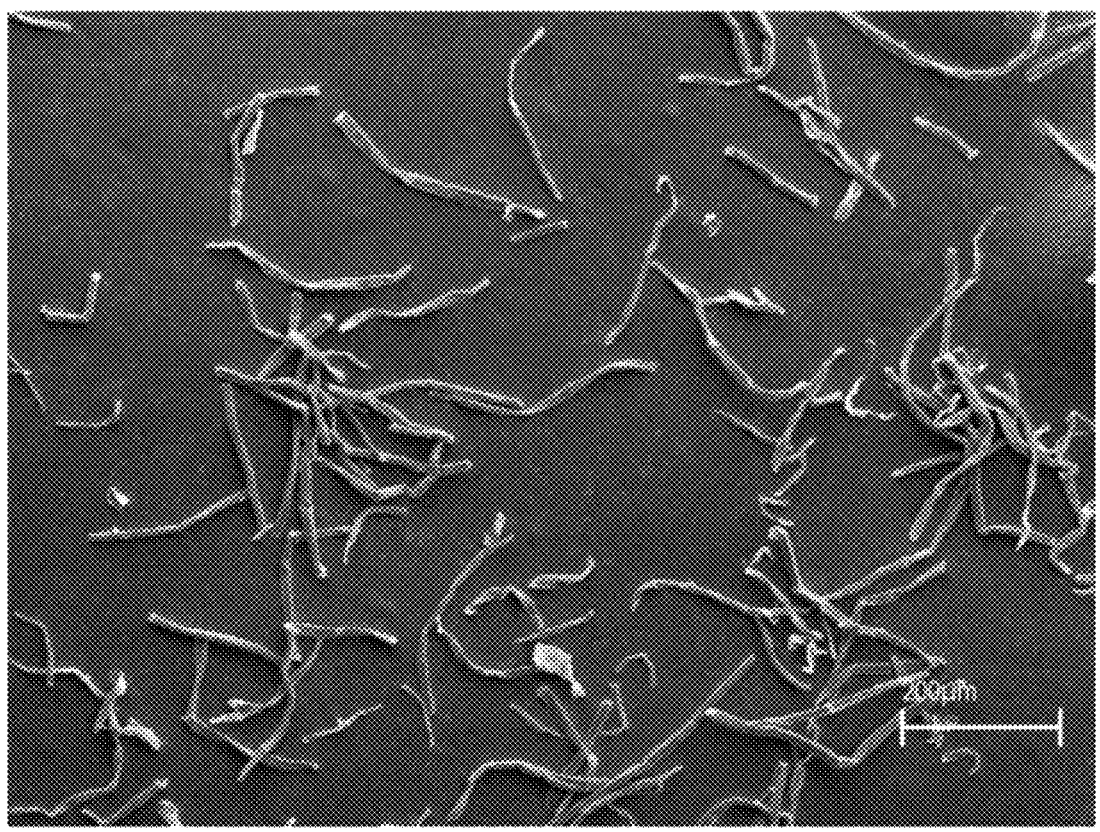
FIG. 8 (A)-(C) shows SEM images of recalcitrant cellulose after 48 hours of enzymatic hydrolysis at enzyme dosage of 2.5 FPU Genencor Multifect B+5 FPU Novozyme 476 (A), at enzyme dosage of 5.0 FPU Genencor Multifect B+5 FPU Novozyme 476 (B), or at enzyme dosage of 10.0 FPU Genencor Multifect B+5 FPU Novozyme 476 (C).
Figure 8B:
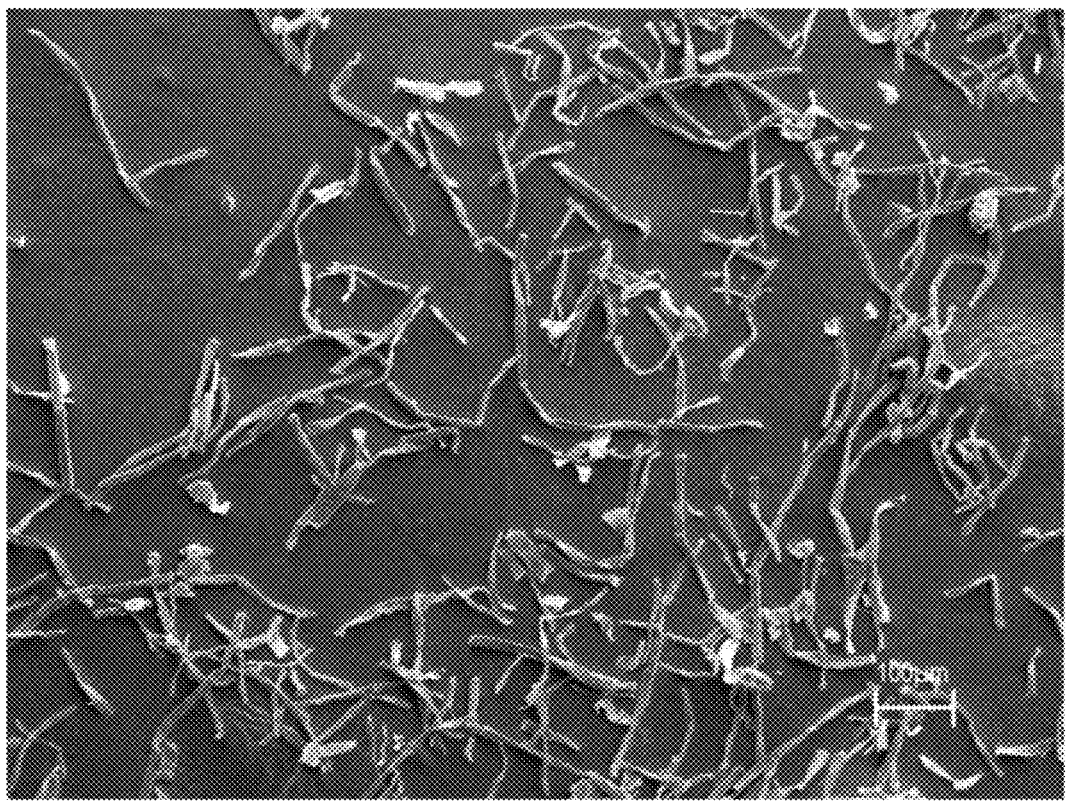
Figure 8C:
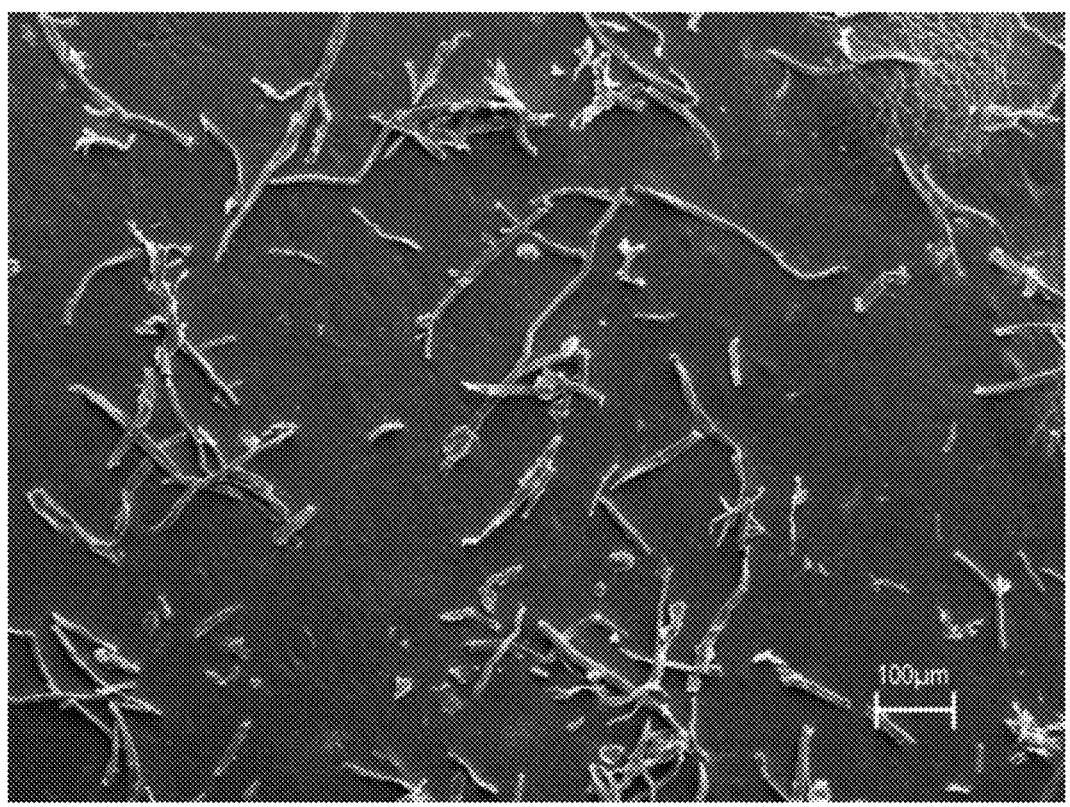

The morphology of the cellulase fractionated recalcitrant cellulosic solids can reveal the physical destructions of the cellulosic fibers by cellulase, which is important to facilitate NFC production using a Microfludizer. Cellulase not only cuts the chain length of cellulose evidenced by the significant reductions in DP throughout the hydrolysis process (FIG. 3), it also significantly shortened the fiber length as hydrolysis proceeded (comparing FIG. 6, original eucalyptus fibers with FIGS. 7 and 8, enzyme pretreated eucalyptus fibers under different conditions). The fiber length was reduced to about 200 μm after 24 hours hydrolysis at enzyme loading of 5 FPU Genencor Multifect B 5 FPU+5 FPU Novozyme 476/g cellulose (FIG. 7c). In addition, cellulase not only reduced the length of long fibers, but also completely hydrolyzed small cellulosic particles and fines, to produce a substrate of good uniformity in length (FIG. 7c and FIG. 8).

Ethanol Production from Hydrolyzed Amorphous Cellulose

Figure 9:
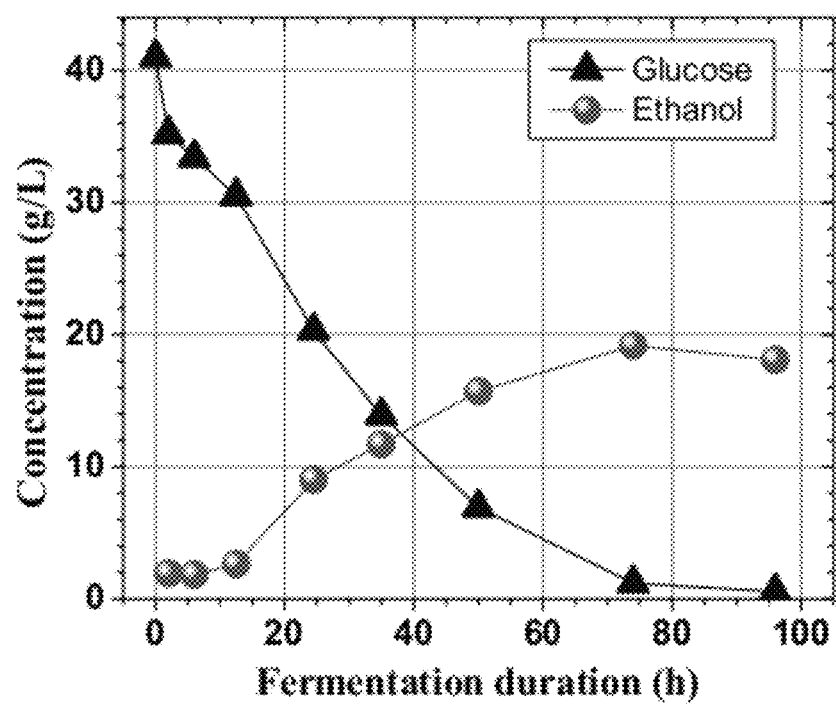
FIG. 9 shows the effect of fermentation duration on the concentrations of glucose and ethanol.

The sugar streams from cellulase hydrolysis can be further hydrolyzed using β-glucosadase to glucose for ethanol production through fermentation. Without the application of xylanase, the resultant sugar stream is simply glucose and was found to be easily fermentable to ethanol using *S. cereviase* D5A (ATCC® Number: 200062) as demonstrated by the measured time-dependent glucose and ethanol concentrations in the fermentation broth (FIG. 9). Glucose consumption and ethanol production in the first 48 h were 0.72 g/L/h and 0.31 g/L/h, respectively. The fermentation efficiency was 91.6% based on measured initial glucose concentration of 41 g/L and terminal ethanol concentration of 19.2 g/L at 72 hours.

Morphology of Nano-Fibrillated Cellulose (NFC)

Figure 10:
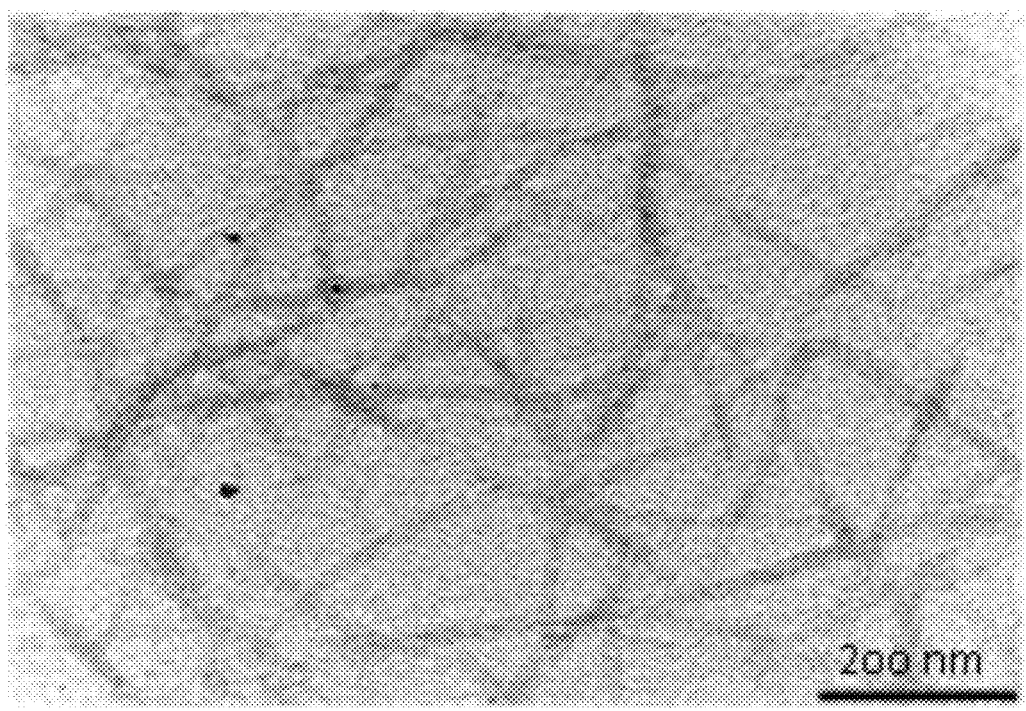
FIG. 10 shows a TEM image of nanocellulose fibers produced from recalcitrant cellulose.

Enzyme-fractionated fibers were homogenized (refined) using a Microfluidizer, which is essentially a specialized homogenizer, and the morphology of the homogenized fibers was examined after incremental levels of homogenization corresponding to discreet numbers of passes through the Microfludizer. After twenty passes through the Microfluidizer with a nozzle size of 200 μm, a significant portion of the fibers were not converted to nanofibers, and fibers with micrometer-sized diameters and with lengths of ten microns or larger. However, after a total of sixty passes (50 passes through a nozzle of 200 μm and 10 passes through a nozzle of 87 μm), large micrometer-sized fiber bundles were no longer present and resulted in nano-fibrillated cellulose with diameter of about 20 nm and length of 500 nm or longer (FIG. 10).

Properties of NFC Films

Figure 11:
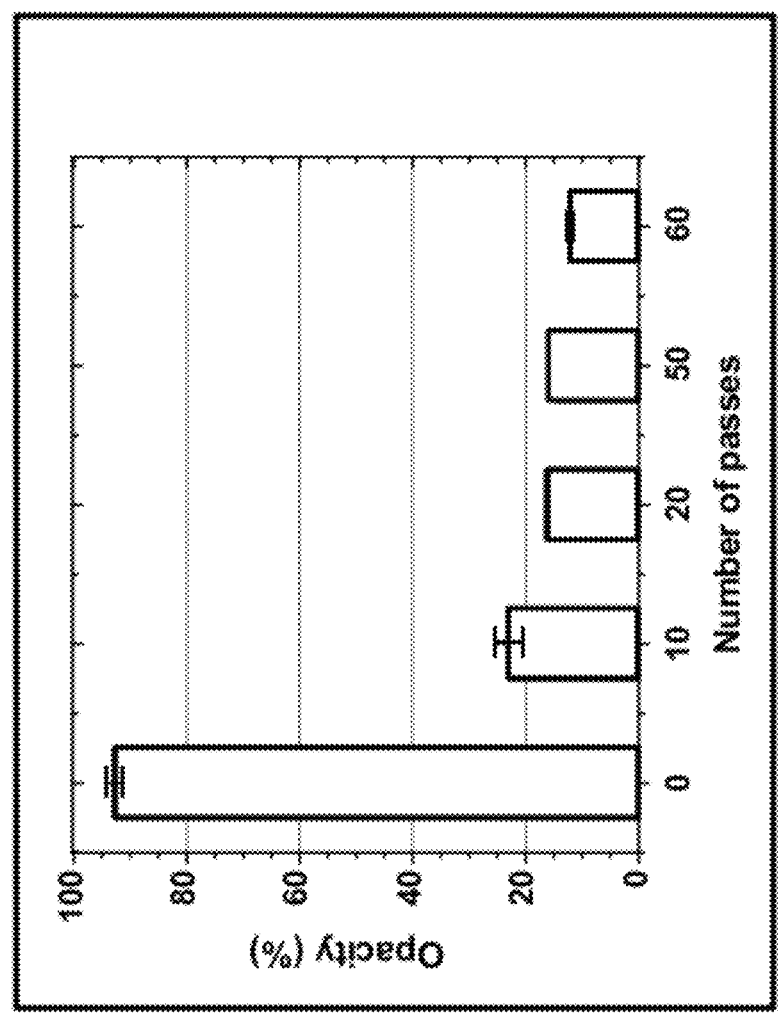
FIG. 11 shows opacity of nanocellulose sheets as a function of passes through a Microfluidizer.
Figure 12:
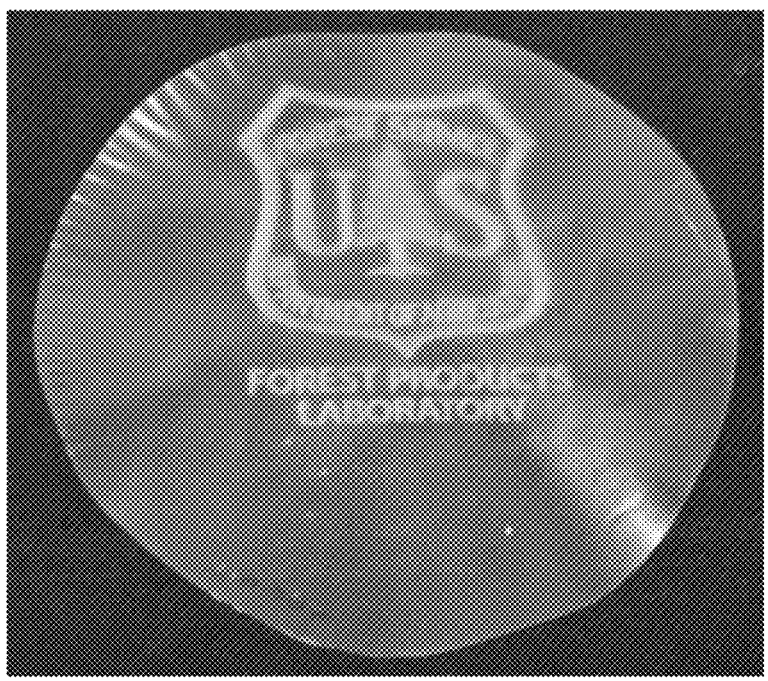
FIG. 12 shows an image of a nanocellulose film produced with a fractionation processes according to the present invention. The logo was placed underneath the nanocellulose film.
Figure 13:
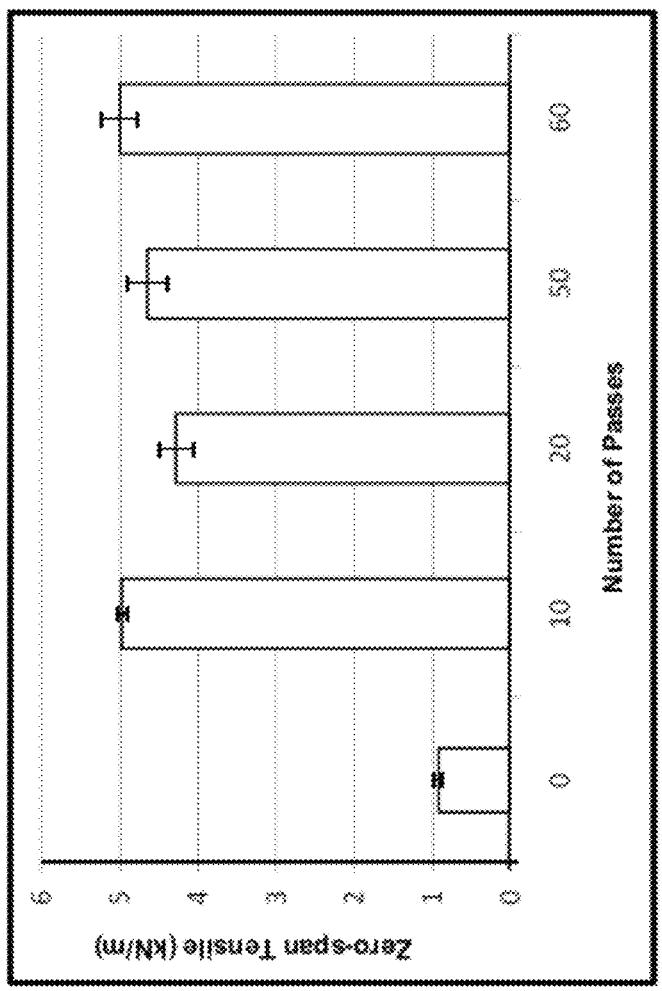
FIG. 13 shows the effect of passes through the microfluidizer on the zero-span tensile strength of films.
Figure 14:
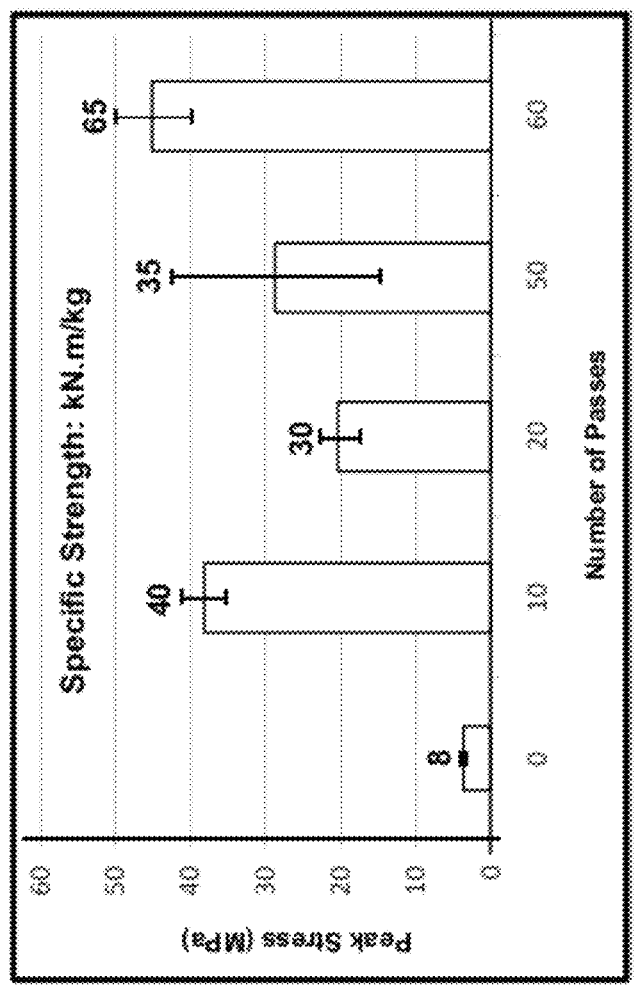
FIG. 14 shows the effect of passes through the microfluidizer on the peak tensile stress strength of films.
Figure 15:
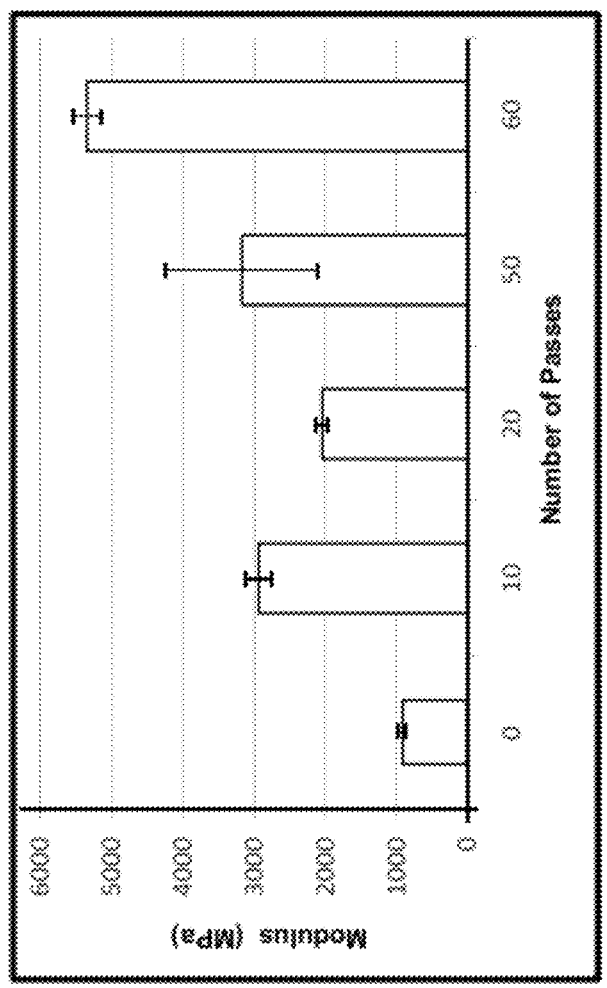
FIG. 15 shows the effect of passes through the microfluidizer on the tensile modulus of films.

Films of the fractionated and microfluidizing homogenized fibers were produced and their optical and mechanical properties were measured as an initial evaluation of the properties and utilities of the NFC. The opacity of the films clearly decreased with the number of passes (as a measure of the degree of homogenization) through the Microfluidizer (FIG. 11). The NFC films, such as the one shown in FIG. 12, produced from highly nano-fibrillated cellulose (60 passes) had opacity values of only approximately 12%. Zero-span tensile strength was markedly improved for sheets made of fibers that had been through the Microfluidizer as few as ten passes compared to purely hydrolyzed fibers without microfluidization (control) (FIG. 13). The zero-span of the NFC film is 5.0±0.2 kN/m, or more than 5 times that produced from the control fibers 0.9±0.1 kN/m. The tensile strength (maximum stress) of the NFC film was 45±5 MPa, or more than an order of magnitude greater than sheets made from the control fibers (3.7±0.3 MPa) (FIG. 14). The modulus of the NFC film was 5400±180 MPa or approximately 6 times that of the sheet made from the control fibers (900±60 MPa) (FIG. 15).

Example 2

Effect of Enzyme Formulation on Nanocellulose Production Using a Bleached Softwood Pulp Material and Chemicals Raw material used in this study was never dried bleached softwood loblolly pine pulp. Pulp was stored at 5° C. before use.

Commercial cellulase Celluclast 1.5 L (complex cellulase) and Fibercare®, an extraglucanase deficient endoglucanase, (Novozymes, Franklinton, N.C.) were both used as received without further purification. All other chemicals used are of ACS reagent grade.

Enzymatic Fractionation

The bleached softwood loblolly pine pulp was directly used for enzymatic fractionation in a 500 mL flask on shaking bed. Endoglucanse and complex cellulase loadings were as listed in Table 1, below.

TABLE 1

|  | SW-0 | SW-1 | SW-2 | SW-3 | SW-4 | SW-5 | SW-G |
|---|---|---|---|---|---|---|---|
| Celluclast 1.5 L (FPU/g substrate) | 0 | 3 | 3 | 3 | 2 | 1 | 0 |
| Fibercare ® (IU/g substrate) | 3 | 0 | 3 | 5 | 1 | 2 | 0 |

Enzymatic fractionation was conducted at a 10% concentration (w/v) of solids at 50° C. for 48 hours using 10 g oven dry pulp and 100 mL buffer solution at pH 4.8. Sodium azide ($NaN_3$) was added to stop microorganism growth at 0.1% loading (w/w) based on oven dry pulp, i.e., 10 g in 1 kg pulp, in oven dry pulp weight. At the end of the incubation, flasks were stored at 5° C. to stop hydrolysis.

The hydrolysate was filtrated through a membrane (Millipore, pore size 0.22 μm, Millipore Corporation, MA) and the filtrate was collected for fermentation study. The retained filtrate cake containing recalcitrant cellulose was washed 2 times with fresh deionized water. The final cake was put into a zip bag and immersed in 80° C. water bath for 30 min to denature remaining cellulase enzymes. The resulting material was used as the starting material for nanofibrillation.

Carbohydrate Determination

The chemical compositions of raw material and enzymatic hydrolysis residuals (recalcitrant cellulose samples SW0, SW1, SW2, SW3, SW4, SW5; original pulp; and mechanically treated sample SW-G) were analyzed by the Analytical Chemistry and Microscopy Lab of the USDA Forest Products Laboratory and the results are shown in Table 2, below:

TABLE 2

| Sample | Ash(%) | K. Lignin(%) | Carbohydrate(%) | | | | | Total Carbo(%) | Total Yield(%) |
|---|---|---|---|---|---|---|---|---|---|
|  |  |  | Arabinan | Galactan | Glucan | Xylan | Mannan |  |  |
| Softwood bleached pulp and SW-G | 0.12 | 0.36 | 0.50 | 0.36 | 79.11 | 8.98 | 6.54 | 95.50 | 95.98 |
| SW-0 | 0.12 | 0.24 | 0.50 | 0.29 | 80.45 | 8.22 | 5.58 | 95.04 | 95.40 |
| SW-1 | 0.25 | 0.37 | 0.37 | 0.22 | 82.42 | 6.05 | 6.58 | 95.64 | 96.26 |
| SW-2 | 0.11 | 0.33 | 0.33 | 0.27 | 79.87 | 6.25 | 6.45 | 93.16 | 93.60 |

TABLE 2-continued

| Sample | Ash(%) | K. Lignin(%) | Carbohydrate(%) | | | | | Total Carbo(%) | Total Yield(%) |
| --- | --- | --- | --- | --- | --- | --- | --- | --- | --- |
| | | | Arabinan | Galactan | Glucan | Xylan | Mannan | | |
| SW-3 | 0.24 | 0.12 | 0.35 | 0.28 | 80.33 | 6.42 | 6.56 | 93.95 | 94.31 |
| SW-4 | 0.00 | 0.33 | 0.33 | 0.27 | 80.45 | 6.28 | 6.55 | 93.88 | 94.21 |
| SW-5 | 0.00 | 0.52 | 0.39 | 0.24 | 82.36 | 6.61 | 6.61 | 96.22 | 96.75 |

Mechanical Pretreatment of the Original Softwood Pulp

The original untreated bleached softwood pulp has an average fiber length of 2.3 mm determined by a fiber analzyer (Kajaani FS-100). This pulp could not be processed directly by the microfluidizer (M-110EH-30 Microfluidics, Newton, Mass.) for nanofibrillation, even at a very low solids consistency of 0.5%.

The untreated pulp was fed into a Supermasscolloider (Masuko Sangyo CO., LTD, Model: MKZA6-2) for mechanical disk milling to reduce fiber length. The gap of the two disks in the microfluidizer was adjusted to −50 μm from the motion zero position, which was determined by slightly contacting the two disks at no load. However, there is no direct contact between the two stone disks with pulp suspension continuously feeding into mill. Pulp suspension at 1.5% solids consistency was passed through the stone disk mill 14 times to complete this mechanical pretreatment step. The mechanically pretreated sample, SW-G, was also nanofibrillated as a control for comparison purpose. The chemical composition of SW-G is the same as the original pulp (Table 2).

Nanofibrillation by Microfluidization

Microfluidization of the recalcitrant cellulose samples (SW-0 to SW-5) and the mechanically pretreated sample (SW-G) were performed at 1.5% solids consistency content using a microfluidizer processor (M-110EH-30 Microfluidics, Newton, Mass.). Fiber suspension passed through the microfluidizer 30 times using a 200 μm chamber, and 20 additional times using a 87 μm chamber to produce nanofibrillated cellulose.

Preparation of Nanocellulose Films

The cellulose nanofibrils produced through microfluidization were diluted to 0.1% w/v using water and continuously stirred for 12 hours using a magnetic stirrer. Nanocellulose film was formed by ultrafiltration of the cellulose nanofibril slurry using a 142-mm Millipore hazardous waste filtration system with polyvinylidene fluoride membrane of 0.22 μm pore size (Millipore, GVWP14250, Ireland). The individual nanocellulose films were blotted by placing the film between filter and blotter papers and pressing at 30 psi for 3 min, and pressing again for another 3 min at 50 psi. The pressed film was then dried overnight in an incubator at 60° C., under a 50 pound load.

Degree of Polymerization (DP) and Crystallinity Index (CrI)

The same method described in Example 1 was used to determine the viscosity of the original bleached pulp, and enzyme fractionated recalcitrant cellulose samples, and the resulting cellulose nanofibrills. DP was calculated from viscosity using different equations based on its value above or below 400 (W. J. Alexander, 1957), as follows:

$$DP^{0.905}=0.75[954\log(x)-325], DP\geq 400 \text{ (Mazumder, Ohtani et al. 2000)}$$

$$DP=120(x)^{1.11}, DP\leq 400$$

where x is pulp viscosity.

The same Raman spectroscopy method for cellulose crystallinity index measurement described in Example 1 was used (Agarwal et al. 2010).

SEM and TEM Imaging

Specimens for scanning electron microscopy (SEM) were prepared by drying drops of the aqueous slurry on polished aluminum mounts. All SEM samples were sputter-coated with gold to provide adequate conductivity. Samples were imaged and photographed using a Leo EVO 40 SEM.

Aqueous nanocellulose samples were diluted using water to solids consistency of approximately 0.1 w/v % for transmission electron microscopy (TEM) at Life Science Microscopy Facility at Purdue University. Each aqueous sample was adsorbed to freshly glow-discharged carbon-coated grids for 30 sec, then rinsed with water, and negatively stained with 0.5% uranyl acetate.

Optical and Mechanical Properties of Nanocellulose Film

The opacities and mechanical properties of the nanocellulose films were measured by TAPPI standard methods as described in Example 1. Stress was measured by tensile tester (Instron 5865, Instron Corporation, Norwood, Mass.). Due to slight slipperiness of the films, film elongation was measured by a laser extensometer (LX1500, MTS Systems Corporation, Eden Prairie, Minn.).

Results

Solids Yields from Enzymatic Fractionation.

Figure 16:
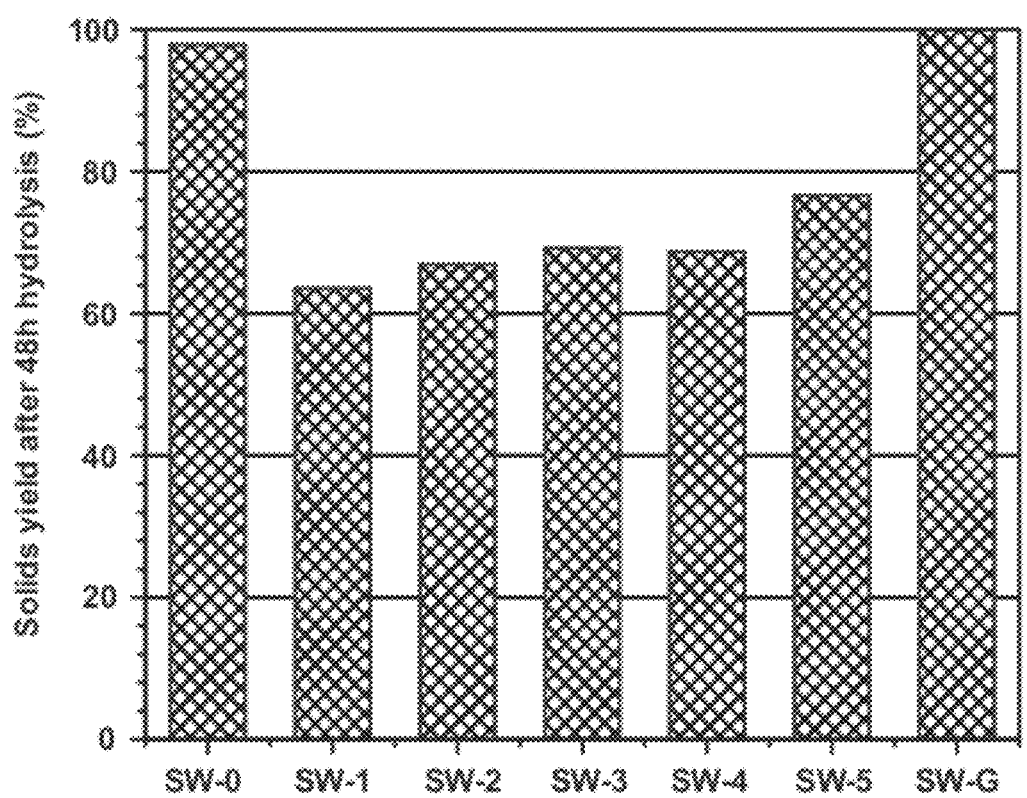
FIG. 16 shows a graph of solids yields from different enzymatic fractionation using different enzyme assays.

Solids yield from the different enzymatic fractionation protocols were compared to the solids yield from the mechanically treated control, SW-G. Solids yield ranged from approximately 60% to nearly 100% of the value for SW-G (FIG. 16). Cellulose dissolution was negligible when only Fibercare® (edoglucanase) was applied (SW0). Cellulose hydrolysis was close to 40% when using Celluclast 1.5 L at 3FPU/g pulp, without additional edoglucanase (SW-1). Cellulose hydrolysis ranged between approximately 20-40% when a combination of enzyme formulations were used, suggesting the degree of cellulose fractionation can be controlled.

Substrate and Nanocellulose Morphologies

Figure 17:
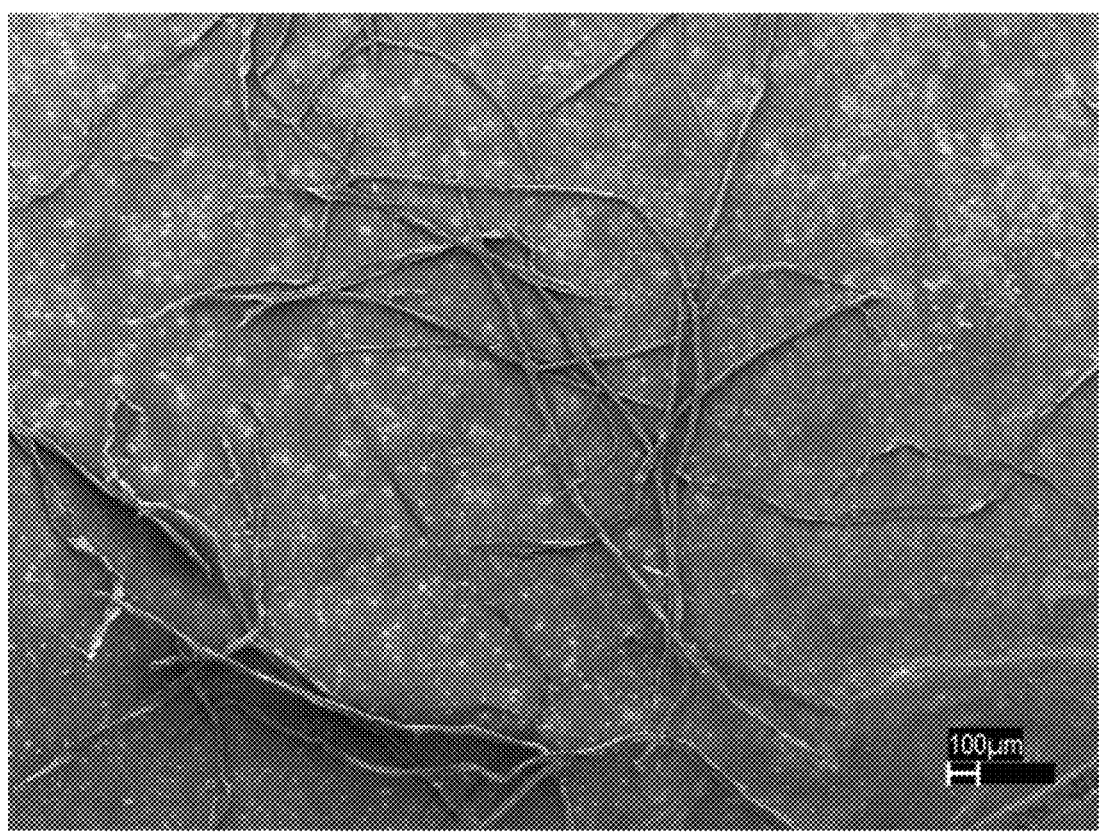
FIG. 17 shows an SEM image of the original bleached loblolly pine pulp fibers. Scale bar=100 μm.
Figure 18A:
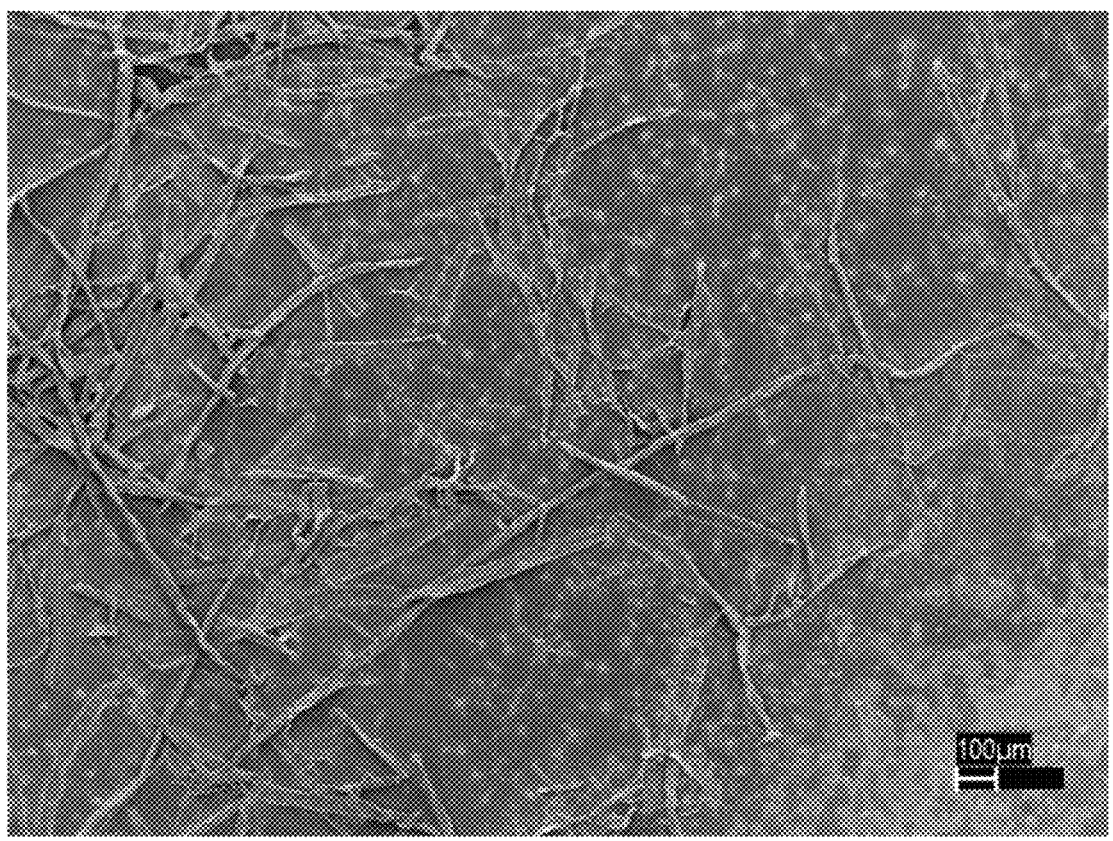
FIGS. 18A-18G show SEM images of enzymatically and mechanically pretreated substrates. (A) SW0; (B) SW1; (C) SW2; (D) SW3; (E) SW4; (F) SW5; (G) SW-G. Scale bar=100 μm for 18A-18F; Scale bar=1 μm for 18G.
Figure 18B:
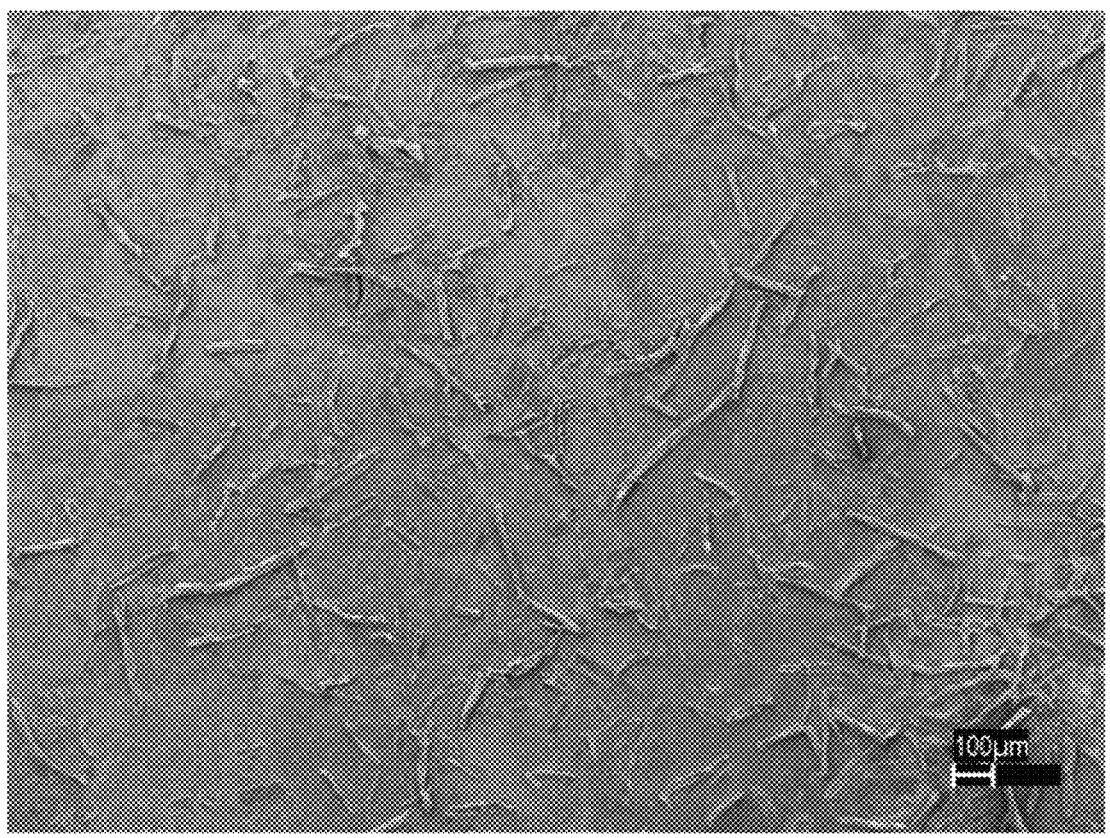
Figure 18C:
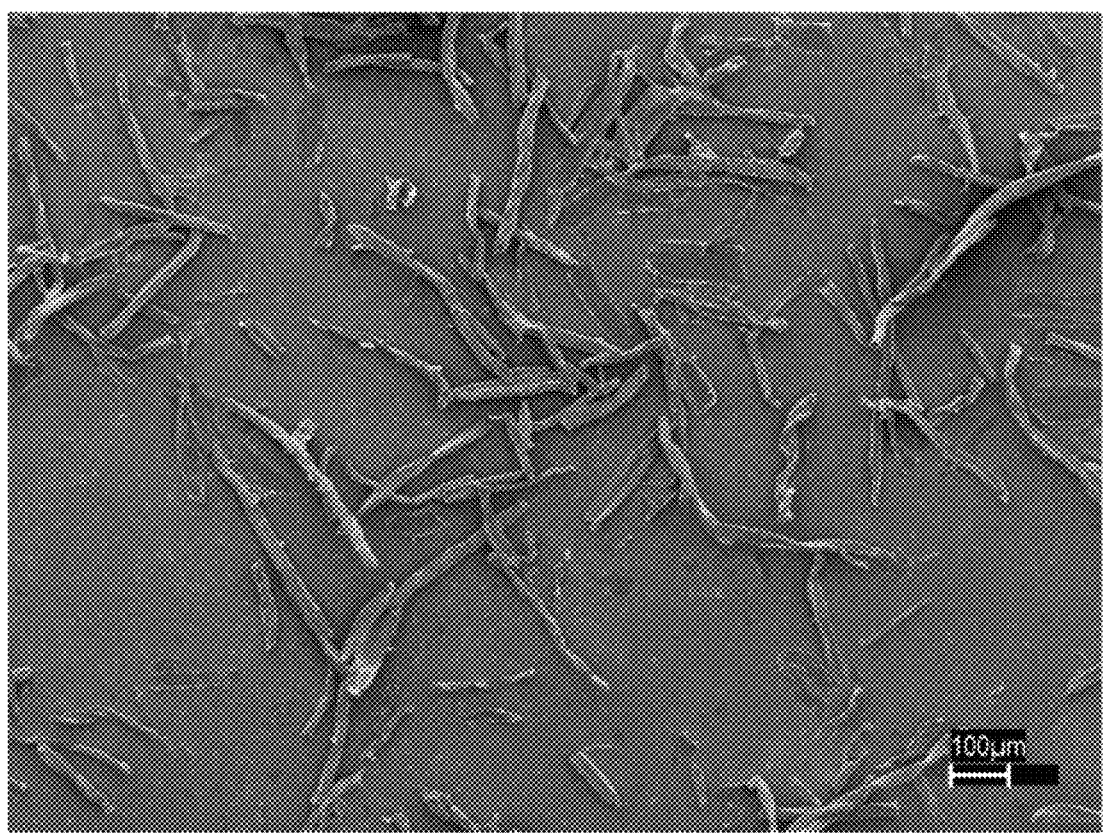
Figure 18D:
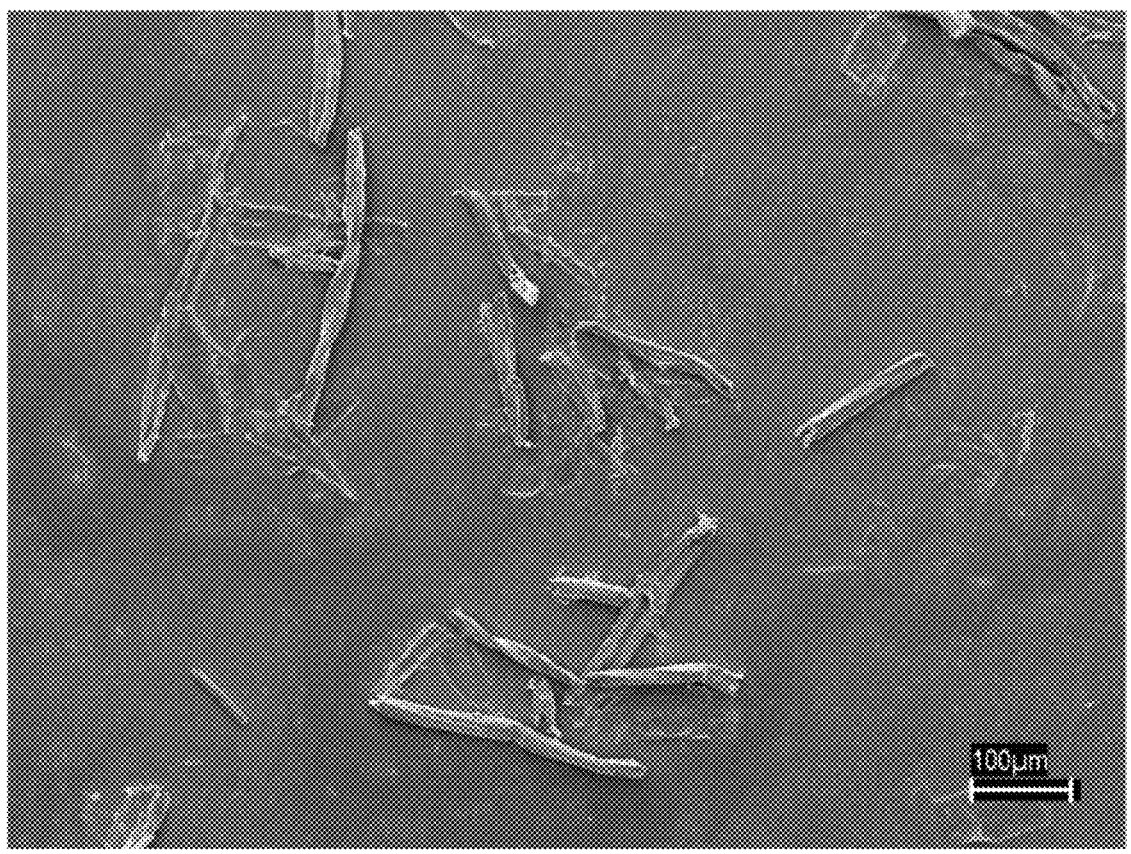
Figure 18E:
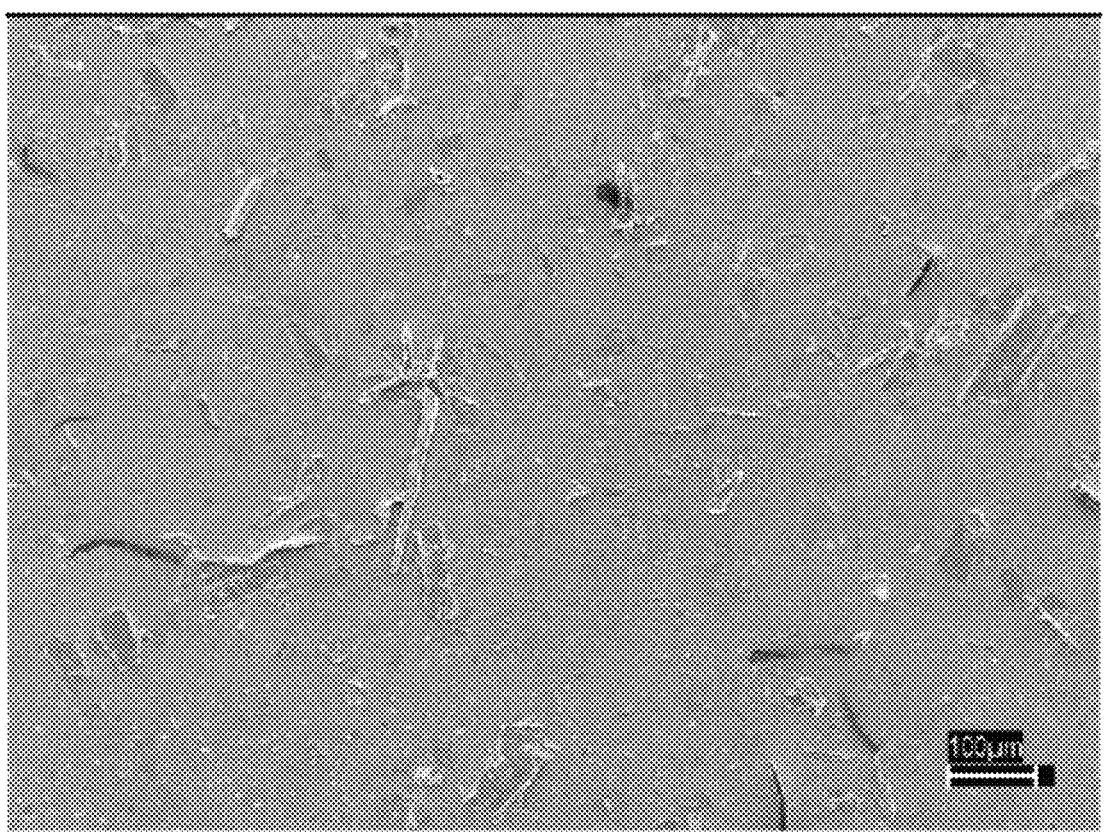
Figure 18F:
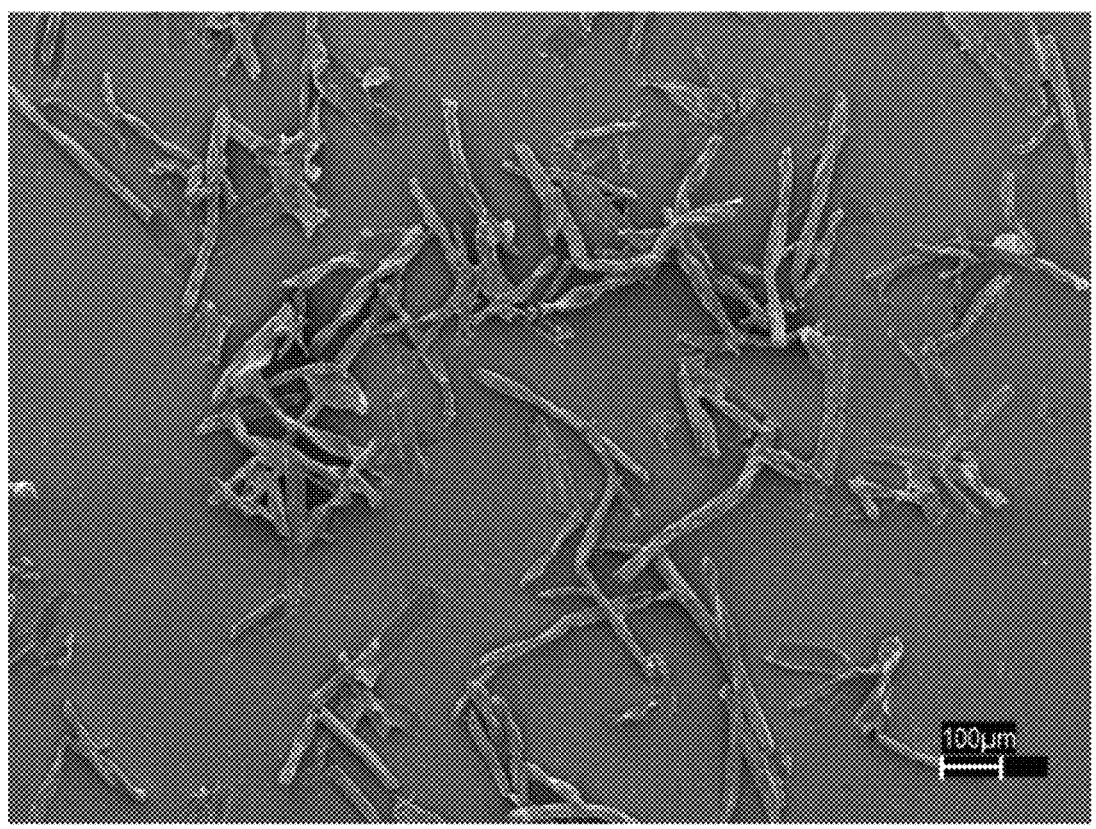

An SEM image of the original bleached loblolly pine pulp indicates typical fiber length around 2 mm, with width of 30 μm (FIG. 17). Enzymatic treatment resulted in a cutting of fibers by the endoglucananse and saccharification by the multiplex enzymes. In general, fiber swelling is visible, with width larger than that of the original pulp fibers. The morphology of the enzyme-fractionated substrates varies with the enzyme formulation applied. When only Fibercare® (endoglucananse) was applied (SW0, FIG. 18A), the fiber degradation was minimal and fibers were simply cut in the amorphous region. Fiber degradation was much more severe when only Celluclast 1.5 L (multiplex) was applied (SW1, FIG. 18B); the fibers were cut much shorter, to approximately 200 μm on average, and degraded cell walls were apparent. When both Fibercare® and Celluclast 1.5 L were both applied (SW2 to SW5; FIGS. 18C-18F), the degrees of fiber cutting were similar to that found in SW1 (when only Celluclast 1.5 L was applied), but the degradation of cell wall was reduced except for SW-4 due to competition between endoglucanase and exoglucanase, as Cellulase 1.5 L was optimized for effective cellulose hydrolysis. The morphology varies slightly among these substrates, depending on the amounts and ratios of Fibercare® and Celluclast 1.5 L applied.

Figure 18G:
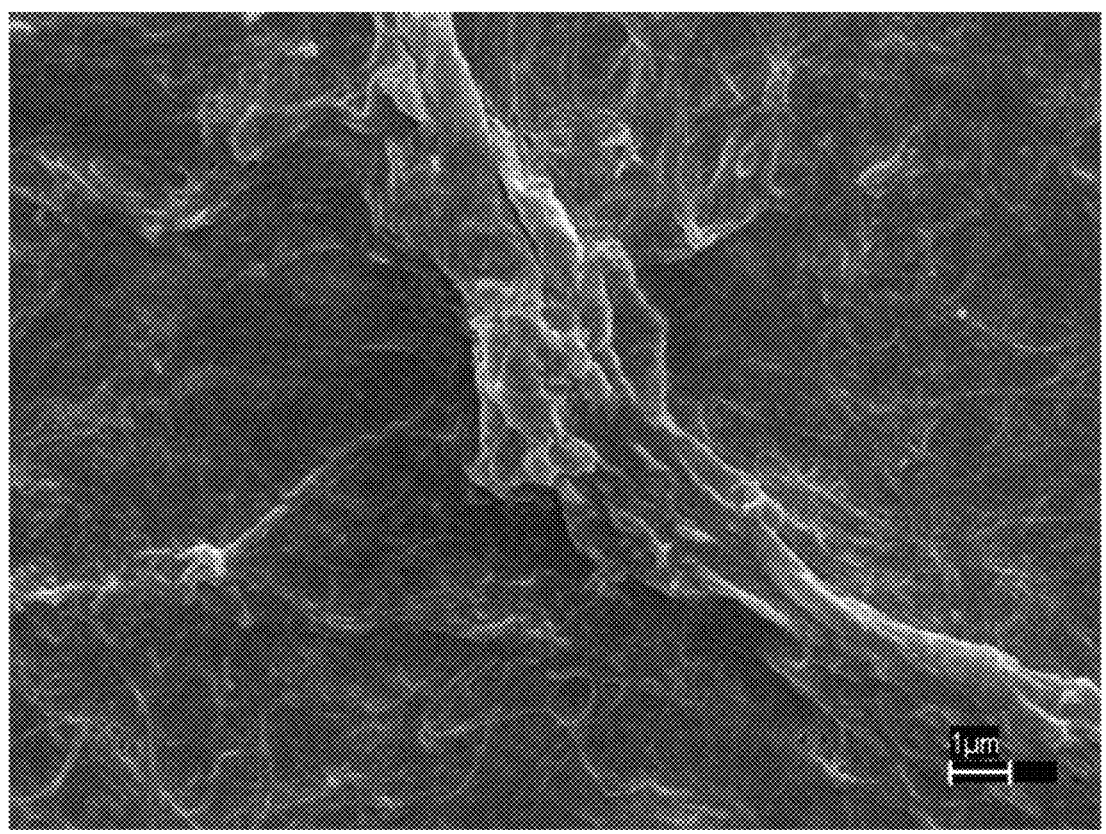

The mechanically pretreated substrate (SW-G, FIG. 18G) has a very different morphology from those of the enzyme treated substrate. It is fibrillated to microfibrils with typical fibril width of 1 µm or less, although microfibers with width of a few micrometers still exist.

The morphologies of the nanofibrillated samples from the six enzyme-fractionated substrates were not much different as straight branched nanocellulose network (FIGS. 19A to 19F); the length of the branches is on the order of 100 to 500 nm for all samples. The width of the branches is quite uniform and approximately 30 nm. This suggests that different enzyme formulations did not cause variation in the morphologies of the resultant nanocellulose.

Figure 19A:
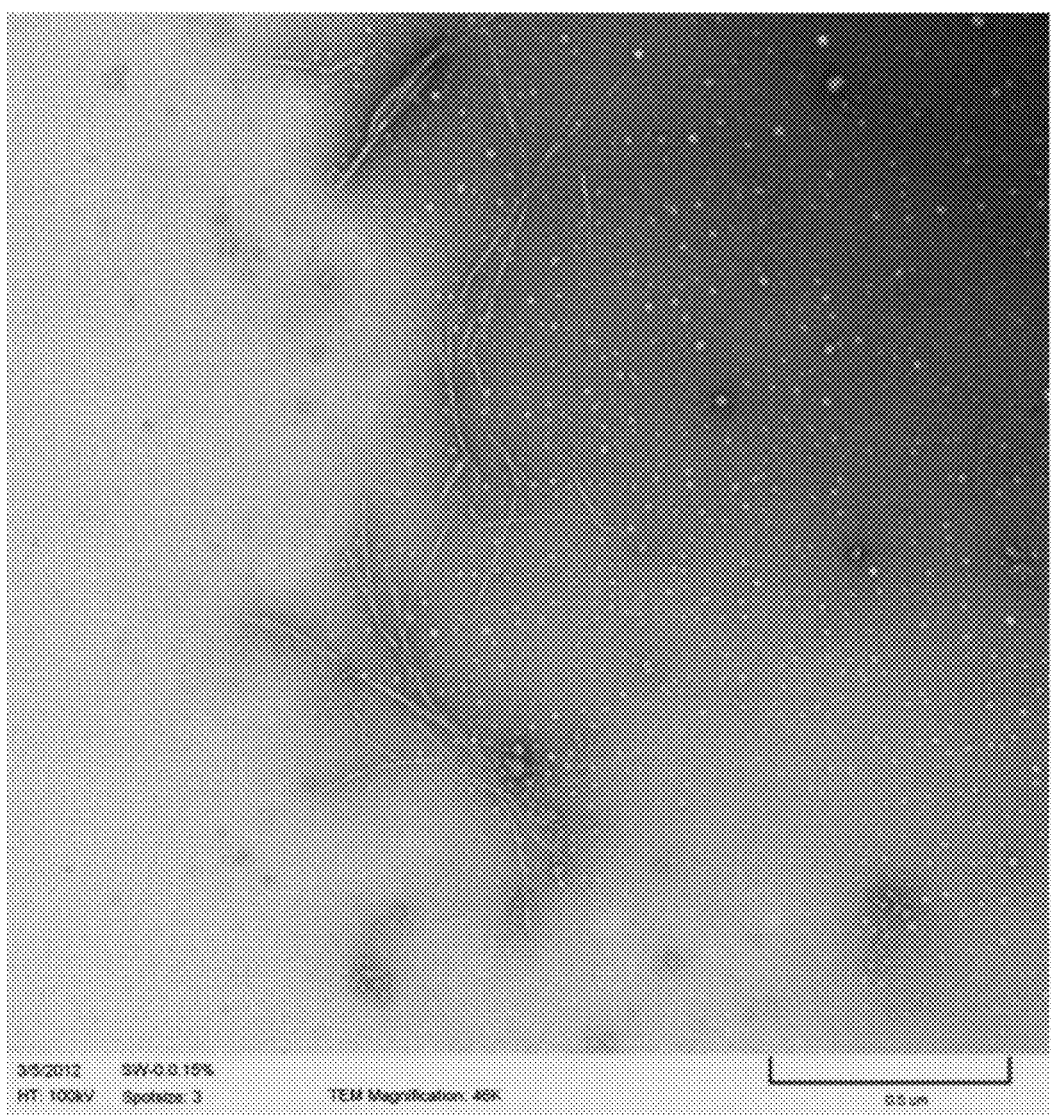
FIGS. 19A-19G show TEM images showing the morphologies of cellulose nanofibrils produced from the substrates shown in FIGS. 18A-18G. (A) SW0; (B) SW1; (C) SW2; (D) SW3; (E) SW4; (F) SW5; (G) SW-G. All scale bars=0.5 μm=500 nm.
Figure 19B:
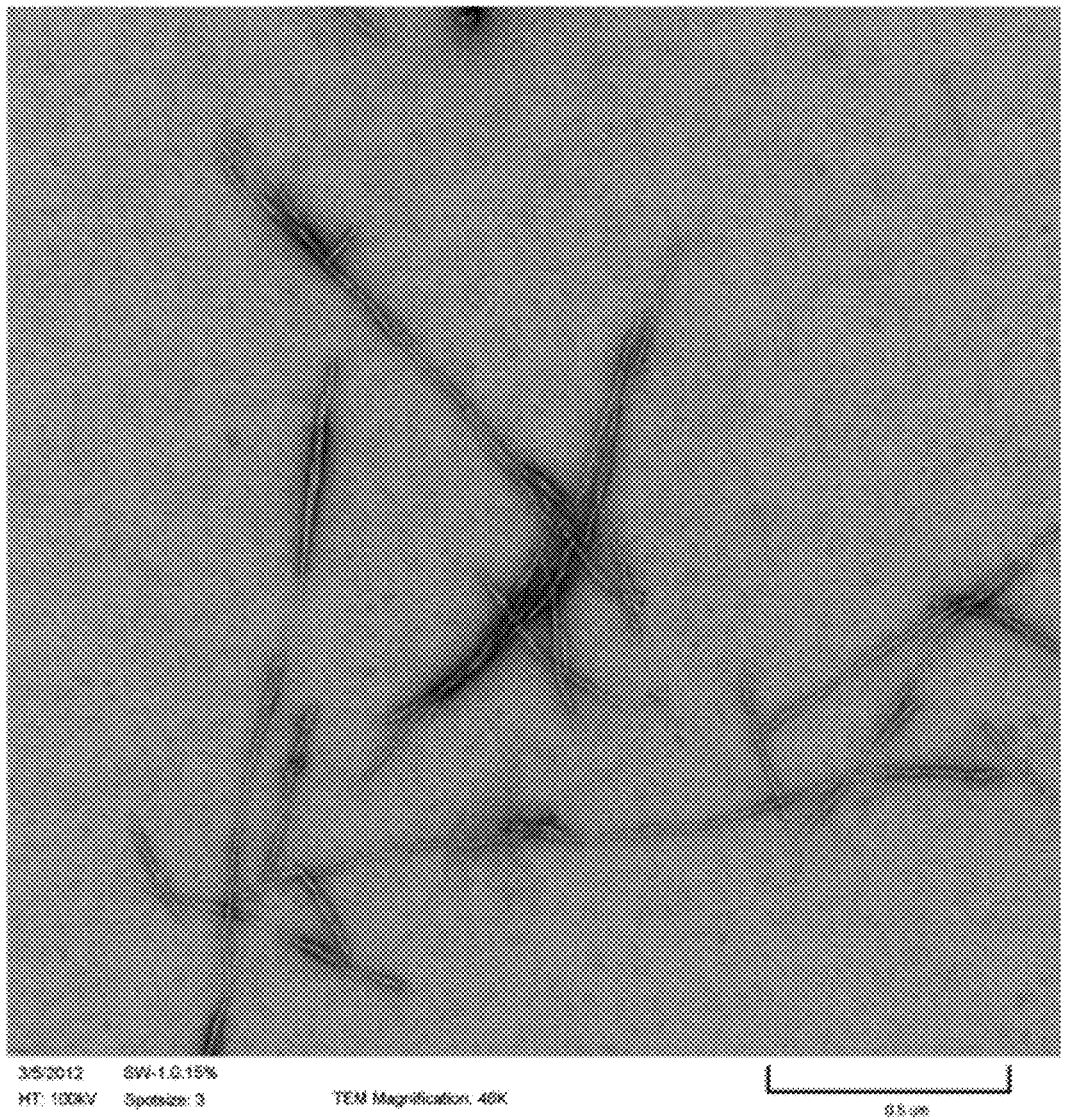
Figure 19C:
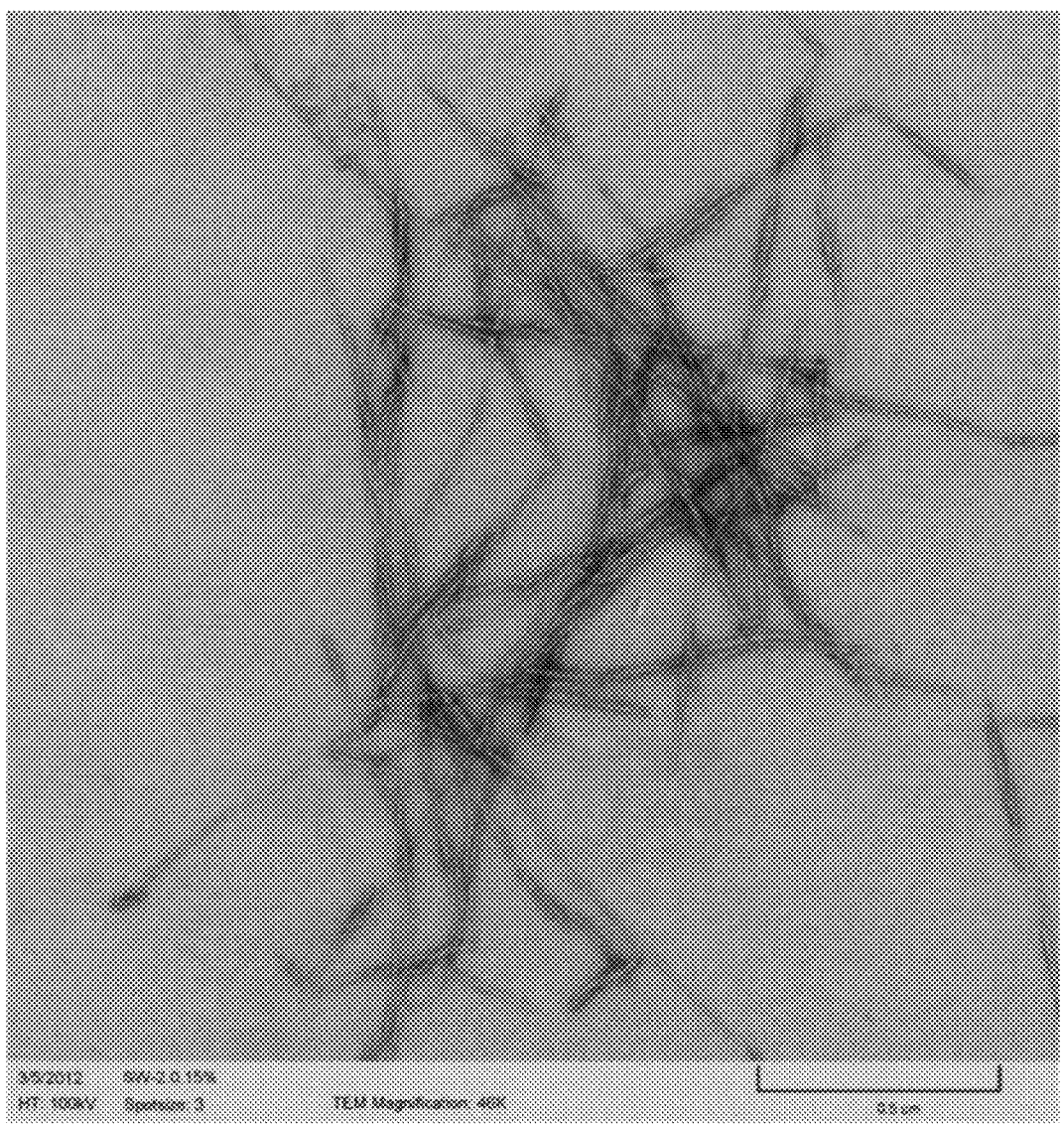
Figure 19D:
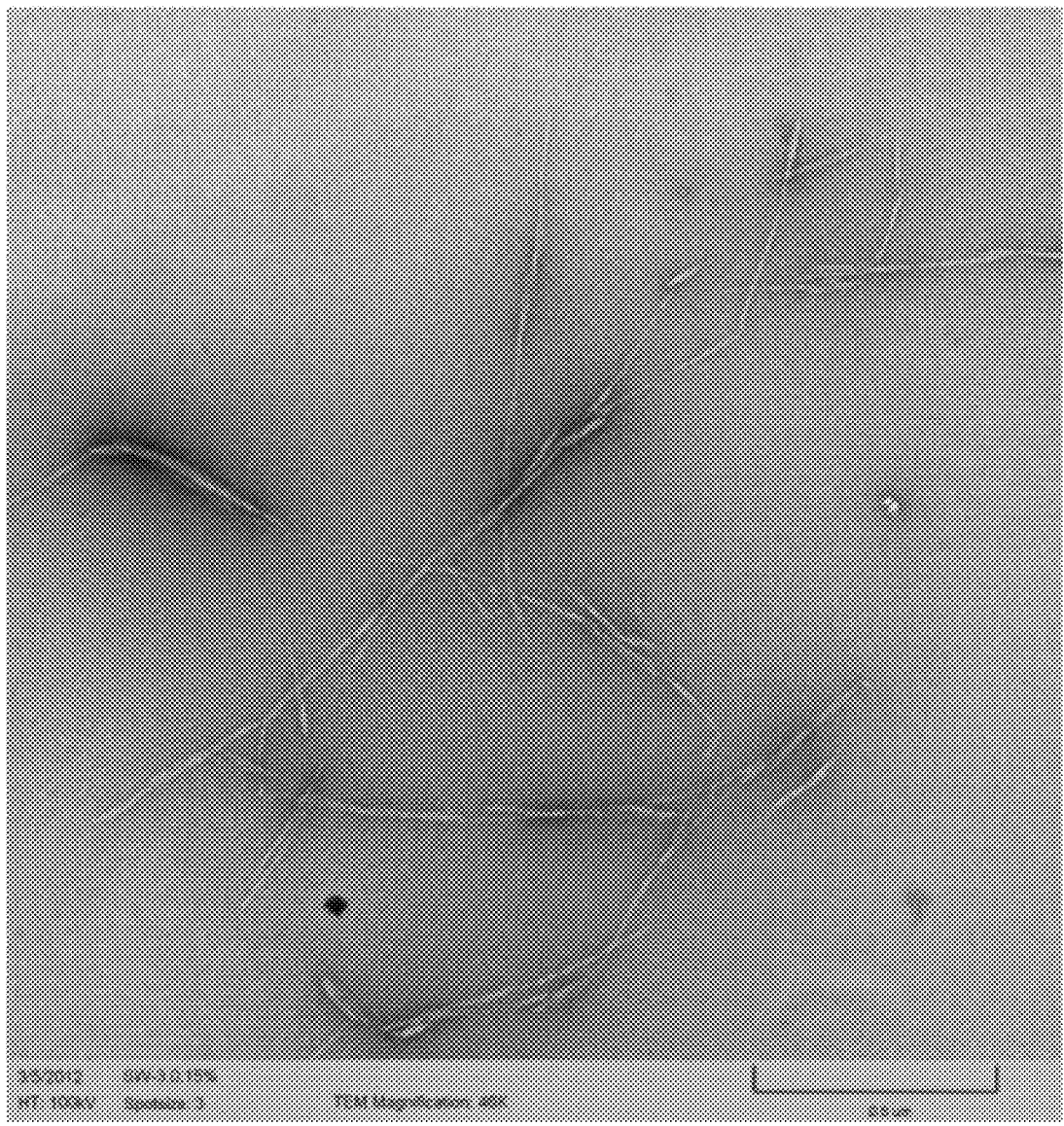
Figure 19E:
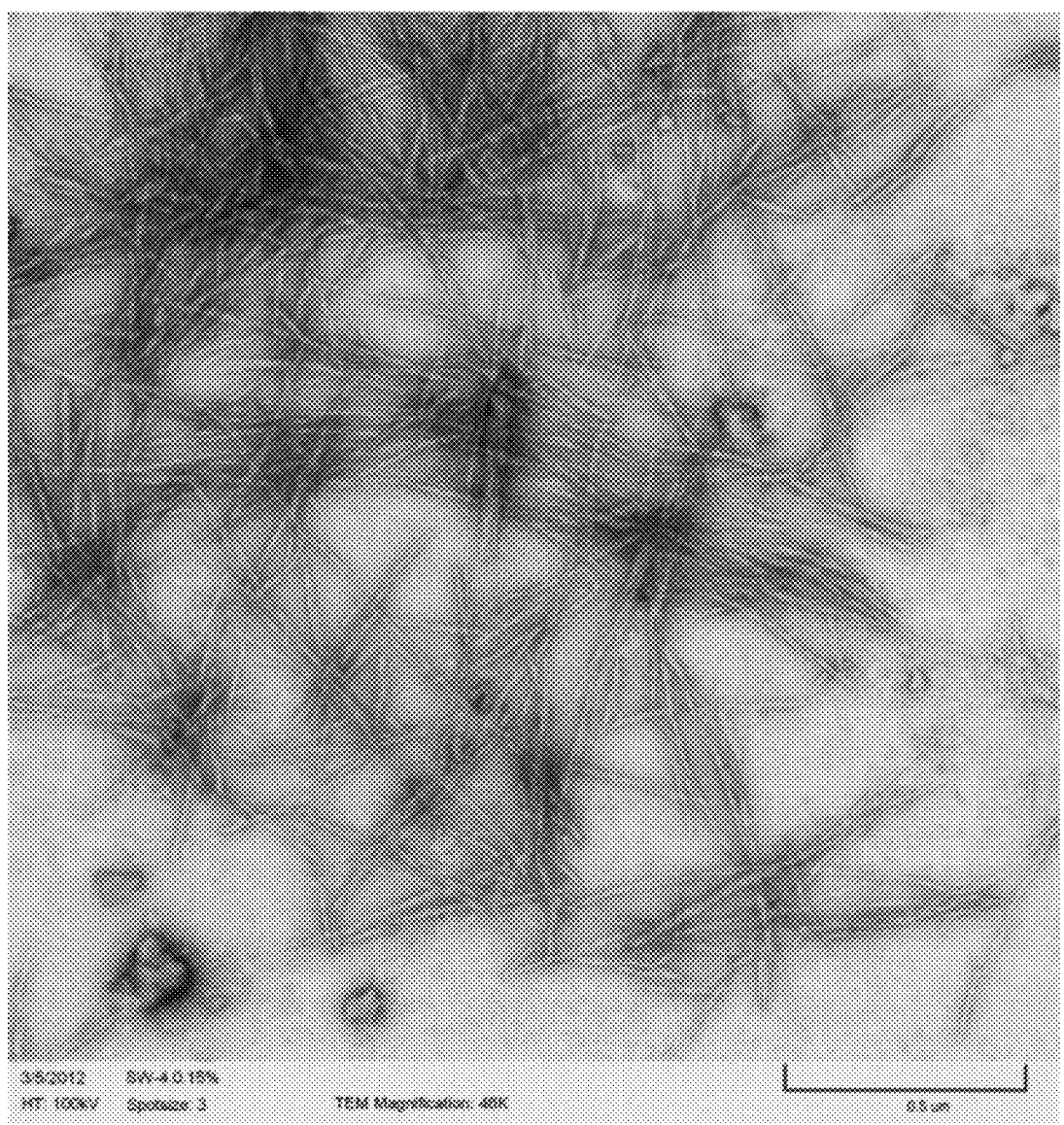
Figure 19F:
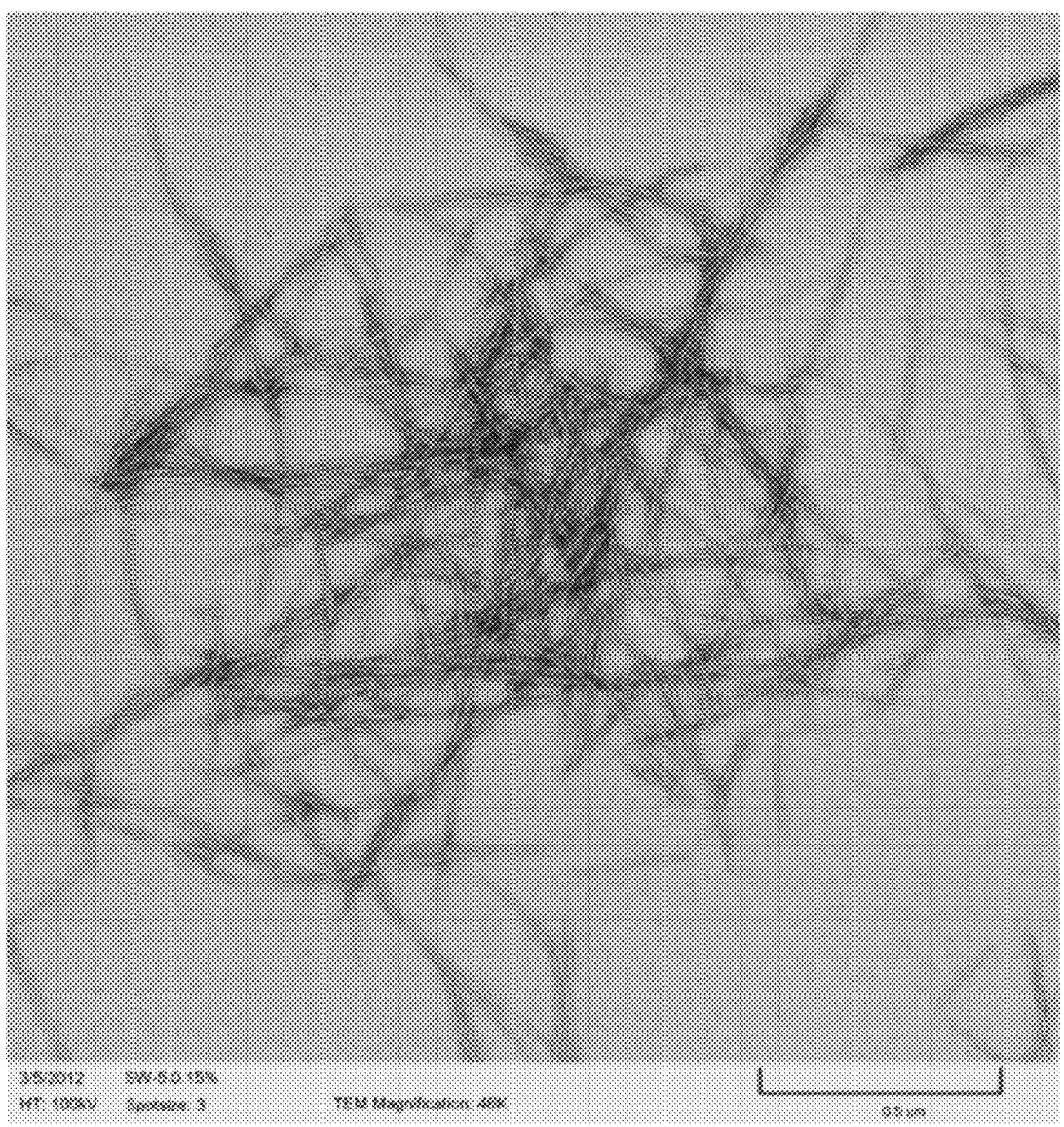
Figure 19G:
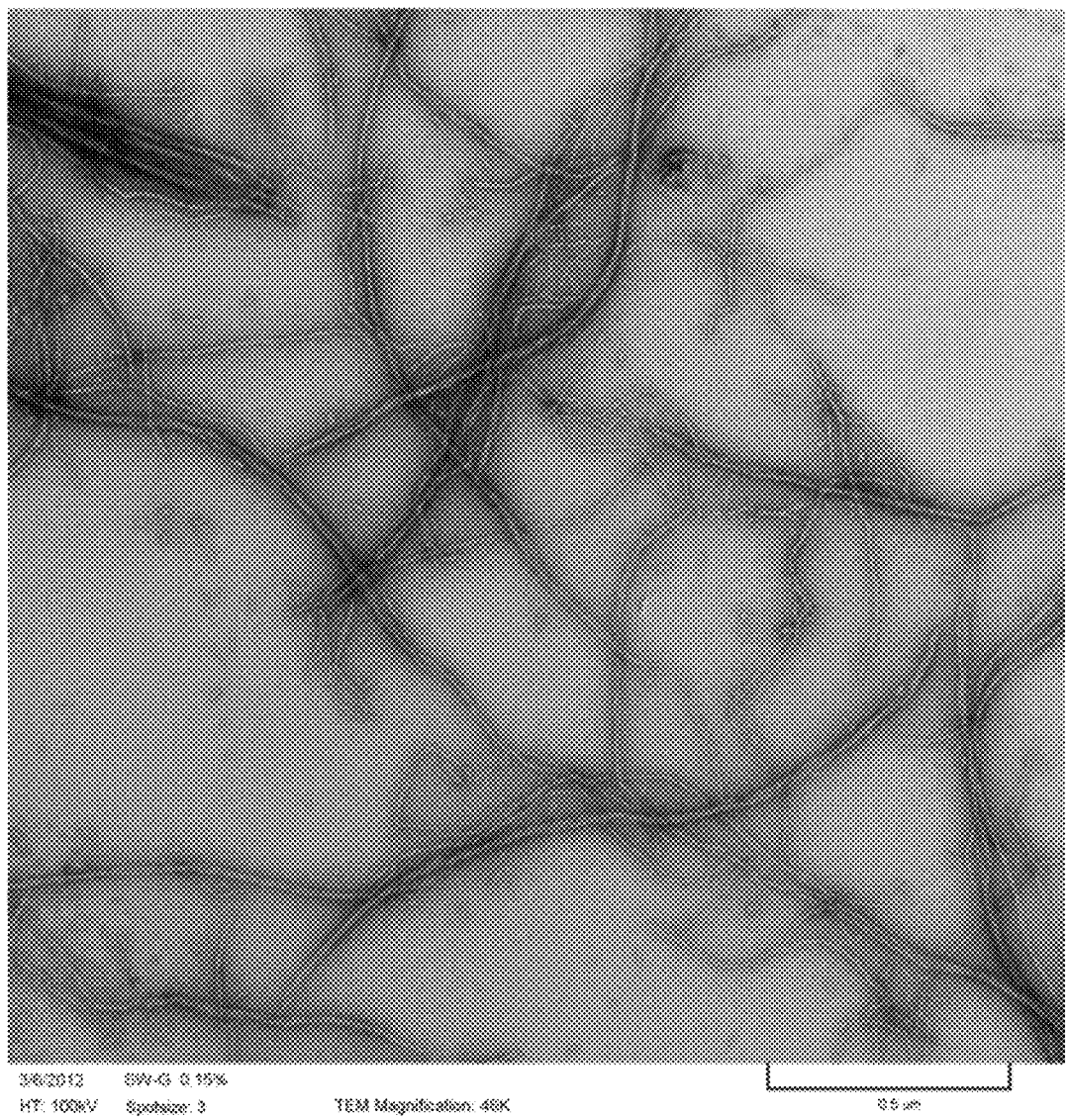

The morphologies of the nanocellulose produced from the mechanical pretreated substrate (SW-G) are very different from the enzyme fractionated samples. The nanofibrils are curved and form an entangled network (FIG. 19G). The width of the nanofibrils varies from the width of elemental fibrils of 3-5 nm to 30 nm. Some of the fibrils are apparently not well separated, as fibril bundles with width 100 nm are observed. The length of some of the fibrils can be over 2 µm. This large fibril network contributes to polymer reinforcement, as discussed below.

Substrate Crystallinity and Degree of Polymerization (DP)

Figure 20:
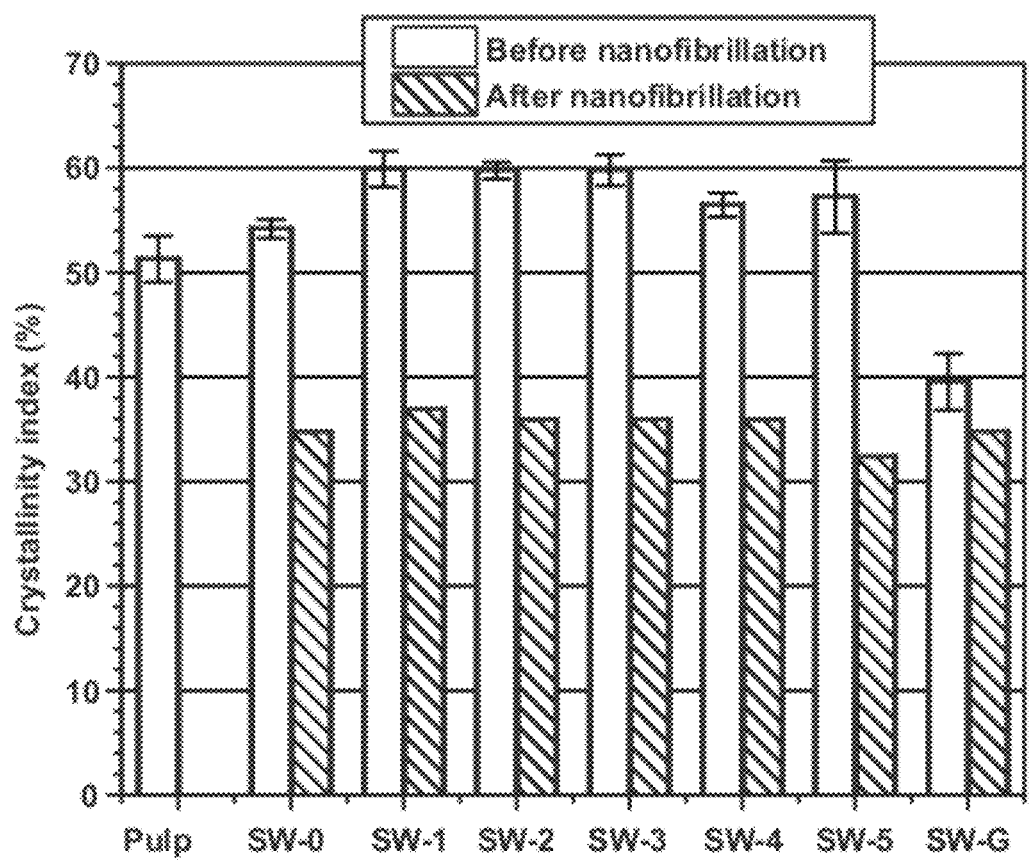
FIG. 20 is a graph showing crystallinity indices of the substrates and cellulose nanofibrills shown in FIGS. 18 and 19. "Pulp" indicates original bleached pulp

Similar to the results presented in Example 1, enzyme fractionation preferentially hydrolyzes amorphous cellulose, which results in a more crystalline recalcitrant cellulose (FIG. 20). The maximal increase in crystallinity in the conditions tested is approximately 20%, similar to that reported in Example 1. The maximal increase occurred with certain levels of Celluclast 1.5 L (multiplex enzyme). The mechanical pretreatment (SW-G) significantly reduced cellulose crystallinity due to milling. Despite the differences in the crystallinity among different feedstock substrates, these differences disappeared after nanofibrillation. The mechanical nanofibrillation resulted in a crystallinity index of approximately 35% for all the cellulose nanofibrils.

Figure 21:
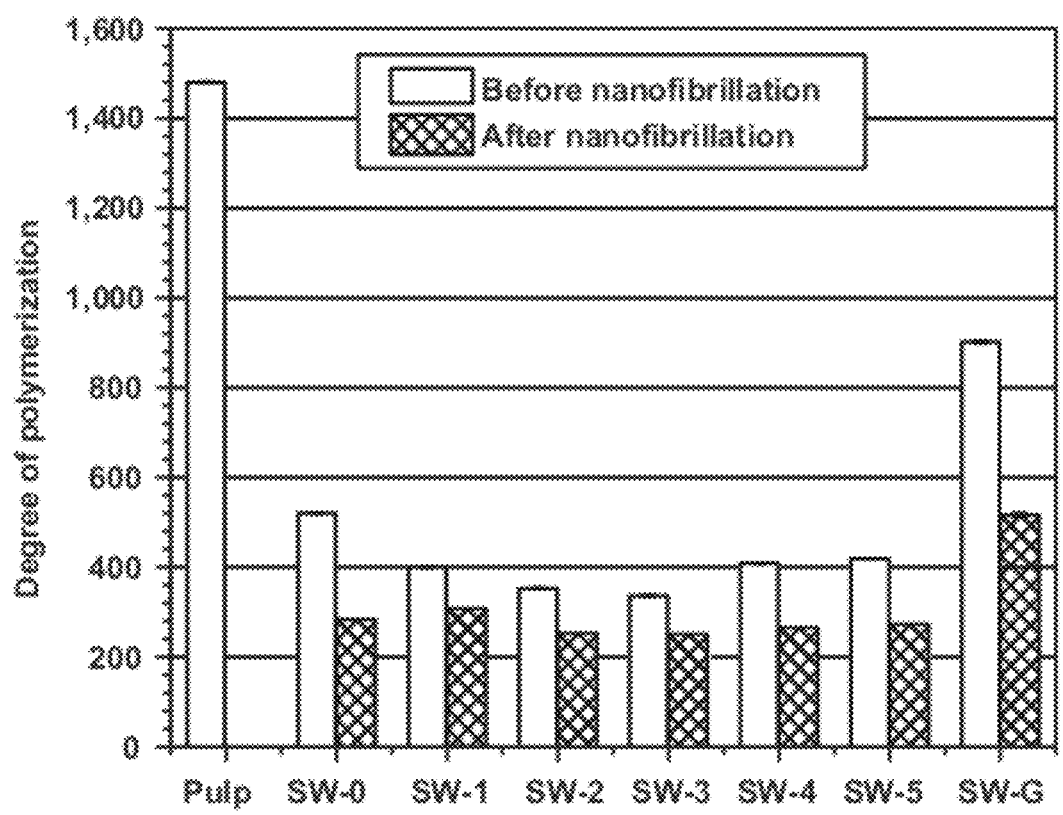
FIG. 21 is a graph showing degree of polymerization of the substrates and cellulose nanofibrills shown in FIGS. 18 and 19. "Pulp" indicates original bleached pulp.

Enzyme fractionation also significantly reduced the cellulose degree of polymerization, from approximately 1500 to 400. The addition of Celluclast 1.5 L (multiplex enzyme) produced a slightly low DP than that observed with endoglucanase alone (FIG. 21). Similar to crystallinity index, the difference in DP disappeared after nanofibrillation for the enzyme fractionated samples, with the DP of the cellulose nanofibrils all at approximately 300. In contrast, the mechanically pretreated sample and its resultant cellulose nanofibril sample have a higher DP than the respective enzyme fractionated samples.

Nanocellulose Film: Optical and Mechanical Properties

The measured opacities of the nanocellulose films produced from different substrates were adjusted for the weights of the different films. The measured opacities were divided by the ratio of the average basis weight of the film in question, over the average basis weight of the film from the mechanically pretreated substrate (SW-G). This is to correct for the mass effect on opacity, as the weight of the films made from different nanocelluloses varied slightly.

Figure 22:
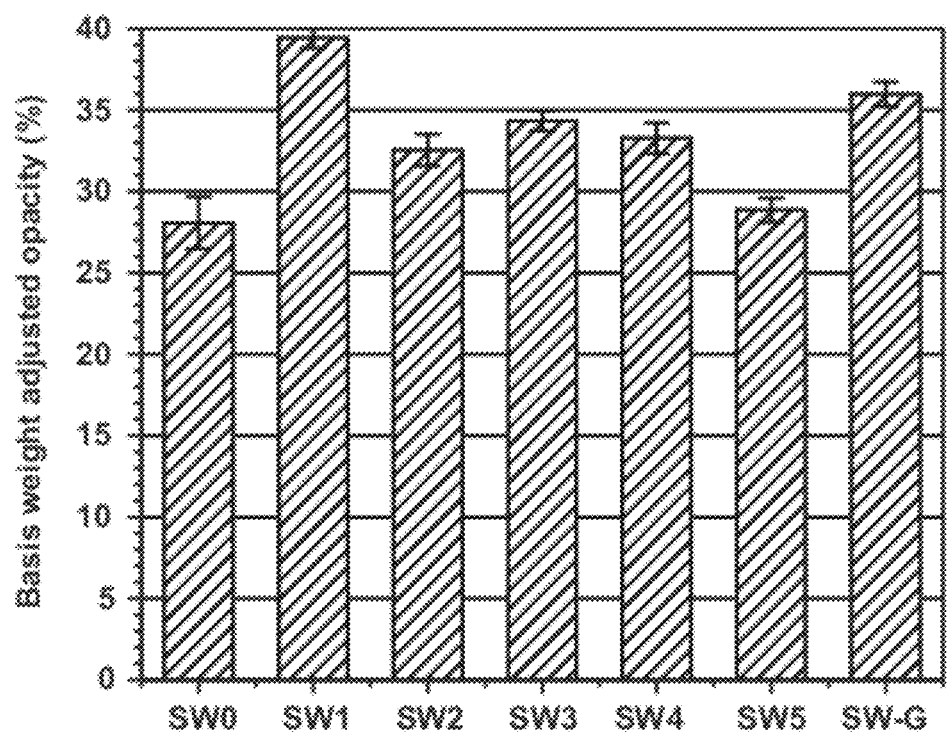
FIG. 22 is a graph showing weight-adjusted opacities of nanocellulose films made from the samples shown in FIGS. 19A-G.

The results indicate that nanocellulose film formed using Celluclast 1.5 L-fractionated substrate tends to have higher opacity than the film produced from the substrate fractionated using endoglucanase (FIG. 22). The film produced from the substrate using endoglucanase alone for fractionation has the lowest opacity.

Figure 23:
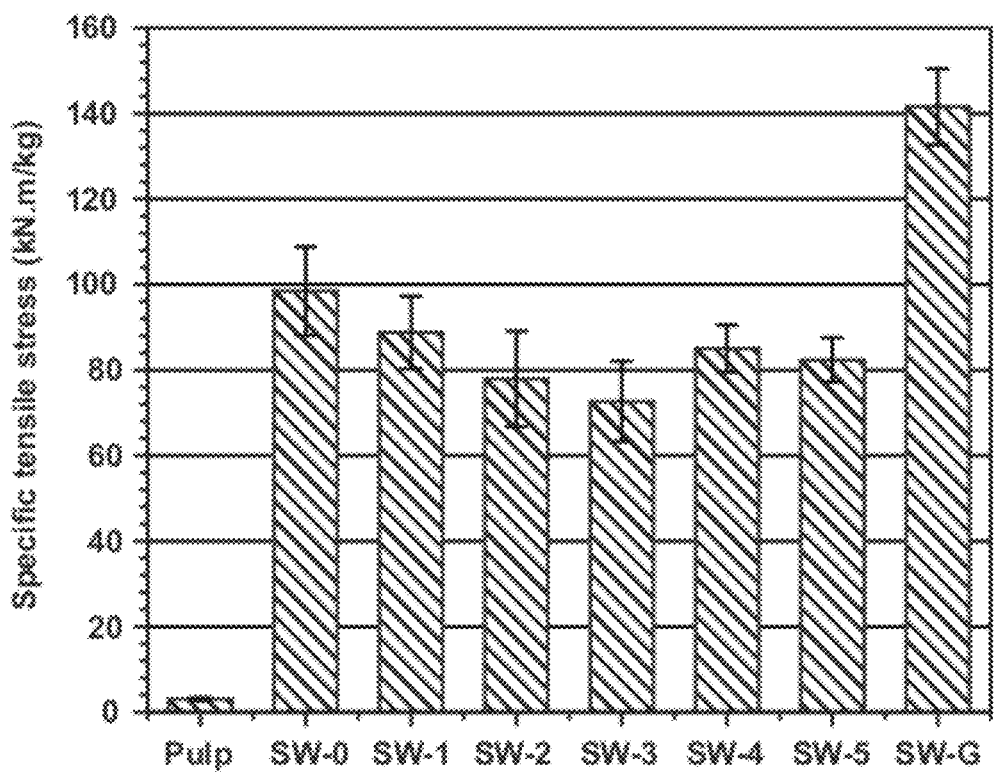
FIG. 23 is a graph showing specific tensile strength of the nanocellulose films made from the samples shown in FIG. 19A-G.

The variations in specific tensile strength of the nanocellulose films from enzyme-fractionated substrates were within measurement uncertainties (FIG. 23). The average specific tensile strength of these films of approximately of 80 (kN.m/kg) are approximately 40 times of that of a handsheet made of unrefined original bleached pulp.

Figure 24:
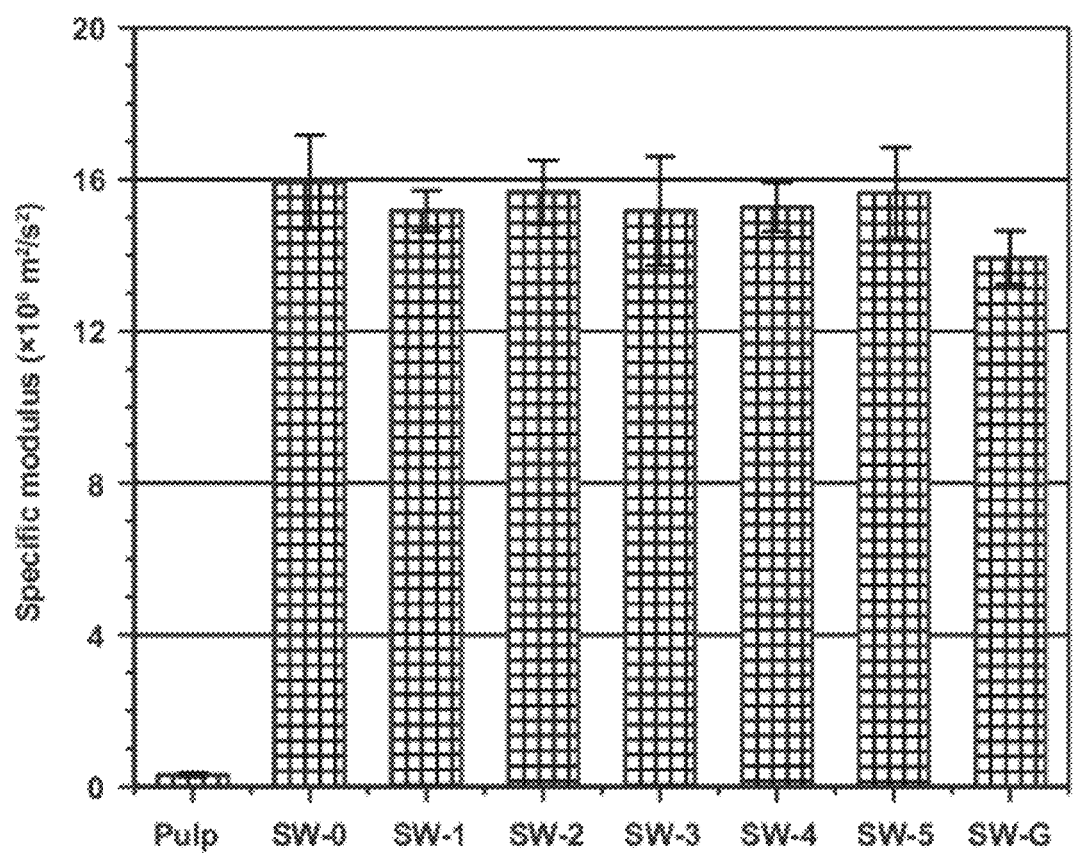
FIG. 24 is a graph showing specific tensile modulus of nanocellulose films made from the samples shown in FIG. 19A-G.

The average specific tensile strength of the film produced from the mechanically-treated substrate is approximately 140 kN.m/kg, with the entangled fibril network observed in FIG. 19G contributing to the improved tensile strength. Notably, the average specific modulus was approximately the same for all nanocellulose films, at $15 \times 10^6$ $m^2/s^2$ (FIG. 24).

The thermal stability of the enzyme-fractionated nanocelluloses was found to be similar to the original fiber, and better than nanocelluloses produces from chemically pretreated material, such as lignocellulosic materials pretreated by TEMPO oxidation.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in fermentation, biofuel, cellulose, and/or micro- and nano-fiber production, agricultural food, feed, and nutrition, or related fields are intended to be within the scope of the following claims.

What is claimed is:

1. A method of producing both biofuel and nano-fibrillated cellulose from a portion of lignocellulosic material comprising:
   a) providing lignocellulosic material and a composition comprising one or more enzymes;
   b) treating the lignocellulosic material with said composition comprising one or more enzymes to produce a product comprising a hydrolyzed sugar and a recalcitrant cellulose;
   c) partitioning said product such that a hydrolyzed sugar fraction is obtained and a recalcitrant cellulose fraction is obtained;
   d) performing a step converting said hydrolyzed sugar fraction so as to generate biofuel; and
   e) conducting a step mechanically processing said recalcitrant cellulose fraction so as to generate nano-fibrillated cellulose.

2. The method of claim 1, wherein said one or more enzymes comprises an enzyme selected from the group consisting of cellulase, complex cellulase of Genencor Multifect B, xylanase, endoxylanase, exoxylanase, beta xylosidase, endomannase, beta-mannosidase, beta-mannase, pectin lyase, pectate lyase, endopolygalacturonase, exopolygalacturonase, rhamnohydrolase, xylogalacturonase, alpha-rhamnosidase, rhamnogalacturonan lyase, xylosidase, arabinofuranosidase, arabinofuranohydrolase, endoarabinase, exoarabinase, endogalactanase, glucuronidase, feruloyl esterase, p-coumaroyl esterase, galactosidase, endoglucanase, exoglucanase, protease, lipase, glucoamylase, cellobiohydrolase, alpha amylase, acetyl esterase, methyl esterase, lignin peroxidase, and laccase.

3. The method of claim 1 wherein said converting comprises fermentation, enzymatic catalysis and/or chemical catalysis.

4. The method of claim 1, wherein said nano-fibrillated cellulose comprises lignocellulose.

5. The method of claim 1, wherein said lignocellulosic material comprises one or more of virgin plant biomass, non-virgin plant biomass, commercial organics, construction and demolition debris, municipal solid waste, waste paper, or yard waste.

6. The method of claim 5, wherein said virgin or non-virgin plant biomass comprises one or more of branches, stems, bushes, canes, corn and corn husks, energy crops, forests, fruits, flowers, grains, grasses, herbaceous crops, leaves, bark, needles, logs, roots, saplings, short rotation woody crops, shrubs, trees, vegetables, fruit peels, vines, sugar beet pulp, wheat middlings, oat hulls, or hard or soft woods.

7. The method of claim 1, wherein said lignocellulosic material comprises one or more of xylan, lignin, protein, beta-glucans, homogalacturonans, and rhamnogalacturonans.

8. The method of claim 1, wherein said lignocellulosic material comprises pulp.

9. The method of claim 8, wherein said pulp is bleached pulp.

10. The method of claim 2, wherein said one or more enzymes consist essentially of one or more of endoglucanase, complex cellulase of Genencor Multifect B, and exoglucanase.

11. The method of claim 1, wherein said nano-fibrillated cellulose comprises fibers having diameters of less than about 1 µm.

12. The method of claim 1, wherein said nano-fibrillated cellulose comprises fibers having diameters of less than about 500 nm.

13. The method of claim 1, wherein said nano-fibrillated cellulose comprises fibers having diameters of between about 10 nm and 300 nm.

14. The method of claim 1, wherein said nano-fibrillated cellulose comprises fibers having diameters averaging about 20 nm and lengths averaging at least 500 nm to 1 or more micrometers.

15. The method of claim 1, wherein said nano-fibrillated cellulose is composed of fibers with diameters averaging less than about 1 µm.

16. The method of claim 1, wherein said nano-fibrillated cellulose is composed of fibers with diameters averaging less than about 500 nm.

17. The method of claim 1, wherein said nano-fibrillated cellulose is composed of fibers having diameters averaging between about 10 nm and 300 nm.

18. The method of claim 1, wherein said nano-fibrillated cellulose consists of fibers having diameters averaging about 20 nm and lengths averaging at least 500 nm to 1 micrometers.

19. The method of claim 1, wherein said lignocellulosic material is not chemically pretreated.

* * * * *